United States Patent
Thiel et al.

(10) Patent No.: US 11,365,289 B2
(45) Date of Patent: *Jun. 21, 2022

(54) ONE-COMPONENT SEALANT OR ADHESIVE COMPOSITION

(71) Applicant: BASF SE, Ludwigshafen am Rhein (DE)

(72) Inventors: Indre Thiel, Ludwigshafen (DE); Thomas Maximilian Wurm, Ludwigshafen (DE); Achim Kaffee, Trostberg (DE); Burkhard Walther, Oldenburg (DE); Bernd Bruchmann, Ludwigshafen (DE); Peter Rudolf, Ludwigshafen (DE); Jens Langhanki, Freiburg (DE)

(73) Assignee: BASF SE, Ludwigshafen am Rhein (DE)

(*) Notice: Subject to any disclaimer, the term of this patent is extended or adjusted under 35 U.S.C. 154(b) by 0 days.

This patent is subject to a terminal disclaimer.

(21) Appl. No.: 17/310,464

(22) PCT Filed: Feb. 10, 2020

(86) PCT No.: PCT/EP2020/053317
§ 371 (c)(1),
(2) Date: Aug. 4, 2021

(87) PCT Pub. No.: WO2020/161355
PCT Pub. Date: Aug. 13, 2020

(65) Prior Publication Data
US 2022/0041907 A1    Feb. 10, 2022

(30) Foreign Application Priority Data
Feb. 8, 2019   (EP) .................... 19156254

(51) Int. Cl.
| | | |
|---|---|---|
| *C09J 133/14* | (2006.01) | |
| *C08F 220/38* | (2006.01) | |
| *C08F 222/10* | (2006.01) | |
| *C08F 222/22* | (2006.01) | |
| *C07F 7/18* | (2006.01) | |
| *C09J 135/02* | (2006.01) | |
| *C08G 77/458* | (2006.01) | |
| *C07D 327/04* | (2006.01) | |
| *C07F 7/08* | (2006.01) | |
| *C08G 71/04* | (2006.01) | |
| *C08G 77/26* | (2006.01) | |
| *C08G 77/28* | (2006.01) | |
| *C09D 183/10* | (2006.01) | |

(52) U.S. Cl.
CPC .......... *C08G 77/458* (2013.01); *C07D 327/04* (2013.01); *C07F 7/0814* (2013.01); *C07F 7/18* (2013.01); *C07F 7/1892* (2013.01); *C08F 220/387* (2020.02); *C08F 222/1063* (2020.02); *C08F 222/22* (2013.01); *C08G 71/04* (2013.01); *C08G 77/26* (2013.01); *C08G 77/28* (2013.01); *C09D 183/10* (2013.01); *C09J 133/14* (2013.01); *C09J 135/02* (2013.01); *C08F 2800/10* (2013.01); *C08F 2800/20* (2013.01); *C08F 2810/20* (2013.01); *C08F 2810/50* (2013.01)

(58) Field of Classification Search
CPC .... C09J 133/14; C09J 135/02; C08F 220/387; C08F 222/1063; C08F 222/22; C08F 2810/20; C08F 2810/50; C08F 2800/10; C08F 2800/20
USPC ........................................... 525/63
See application file for complete search history.

(56) References Cited

U.S. PATENT DOCUMENTS

| | | | | |
|---|---|---|---|---|
| 3,632,557 | A | * | 1/1972 | Brode et al. ........... C08G 18/10 528/28 |
| 3,971,751 | A | | 7/1976 | Isayama et al. |
| 4,625,012 | A | | 11/1986 | Rizk et al. |
| 6,103,850 | A | | 8/2000 | Reichel et al. |
| 6,355,127 | B1 | | 3/2002 | Mahdi et al. |
| 2019/0352461 | A1 | * | 11/2019 | Huber ................ C08G 18/4692 |
| 2020/0354333 | A1 | | 11/2020 | Rudolf et al. |

FOREIGN PATENT DOCUMENTS

| | | | | |
|---|---|---|---|---|
| EP | 1 506 964 | | 2/2005 | |
| EP | 1506964 A1 | * | 2/2005 | ............. C08G 75/28 |
| EP | 2468791 A1 | * | 6/2012 | ......... C08G 59/1411 |

(Continued)

OTHER PUBLICATIONS

U.S. Appl. No. 16/639,339, filed Feb. 14, 2020, 2020/0354333, Rudolf et al.

(Continued)

*Primary Examiner* — Michael M. Bernshteyn
(74) *Attorney, Agent, or Firm* — Grüneberg and Myers PLLC

(57) ABSTRACT

A process prepares a prepolymer containing a urethane group and a curable silicon-functional group, or a prepolymer of formula (IV),

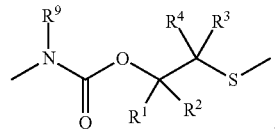

The prepolymer may be cured to a cross-linked polymer by ambient moisture and is therefore suitable for use as a component in a one-component sealant or adhesive composition.

18 Claims, 1 Drawing Sheet

(56) References Cited

FOREIGN PATENT DOCUMENTS

| WO | WO-2012/003187 A1 | 1/2012 | | |
|----|-------------------|--------|---|---|
| WO | 2018/042030 | 3/2018 | | |
| WO | WO-2018042030 A1 * | 3/2018 | ......... | C08G 18/4692 |
| WO | WO-2019/034468 A1 | 2/2019 | | |
| WO | WO-2019/034469 A1 | 2/2019 | | |
| WO | WO-2019/034470 A1 | 2/2019 | | |
| WO | WO-2019/034473 A1 | 2/2019 | | |

OTHER PUBLICATIONS

International Search Report dated Apr. 30, 2020 in PCT/EP2020/053317.
Written Opinion dated Apr. 30, 2020 in PCT/EP2020/053317.
Reynolds et al., "*Mercaptoethylation. II. Preparation of 2-Mercaptoethyl Carbarnates and Oligoethylene Sulfides*," Journal of Organic Chemistry, vol. 26, No. 12, Dec. 1961, pp. 5111-5115.
U.S. Office Action dated Jan. 24, 2022 in U.S. Appl. No. 17/428,705, 7 pages.
U.S. Office Action dated Mar. 28, 2022 in U.S. Appl. No. 16/639,204, 14 pages.
U.S. Office Action dated May 6, 2022 in U.S. Appl. No. 16/639,339, 15 pages.

* cited by examiner

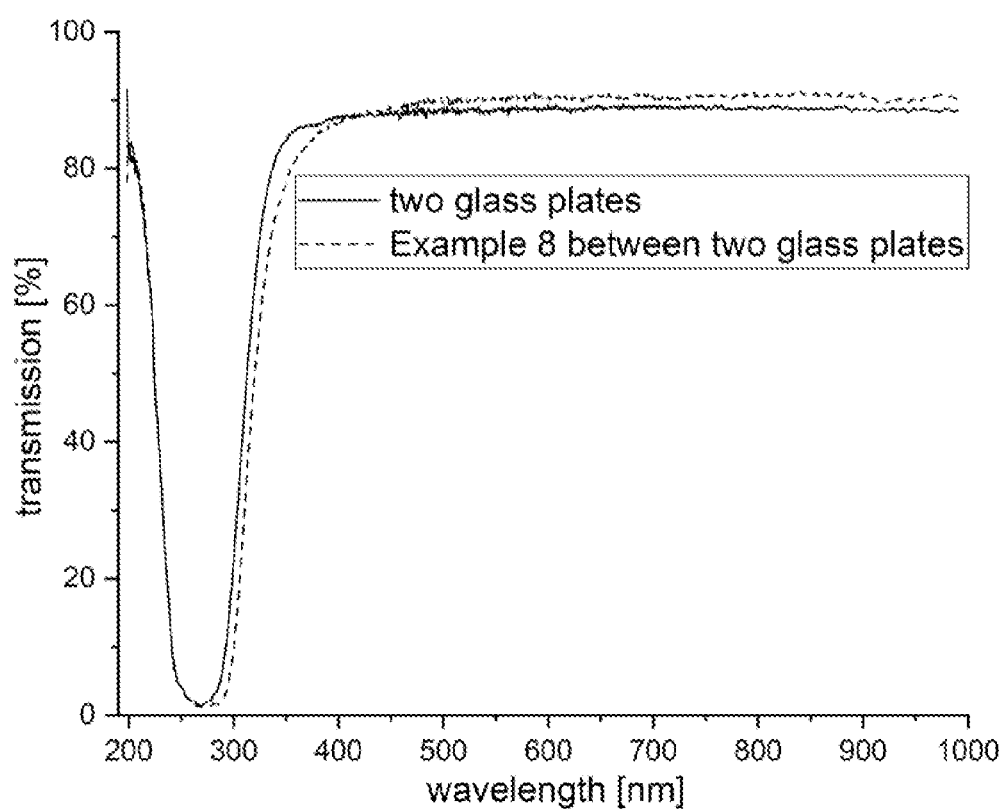

ONE-COMPONENT SEALANT OR ADHESIVE COMPOSITION

CROSS-REFERENCE TO RELATED APPLICATIONS

This application is the National Stage entry under § 371 of International Application No. PCT/EP2020/053317, filed on Feb. 10, 2020, and which claims the benefit of priority to European Application No. 19156254.5, filed on Feb. 8, 2019. The content of each of these applications is hereby incorporated by reference in its entirely.

BACKGROUND OF THE INVENTION

Field of the Invention

The present invention relates to a process for preparing a prepolymer comprising a urethane group and a curable silicon-functional group; a prepolymer comprising said groups, and the use thereof as a component of a one-component sealant or adhesive composition. Further the invention relates to a cross-linked polymer comprising a urethane group and a siloxane linkage having a content of 0.001 to 0.3 mol silicon per 100 g of the cross-linked polymer and to a process for preparing a cross-linked polymer comprising a urethane group and a siloxane linkage.

Description of Related Art

Polyurethanes are important industrial polymers. They have very good mechanical properties and are, therefore, used in many technical applications, for example, as a foam or as a binder or resin in coatings or adhesives.

Polyurethanes have been modified with silyl groups, which are notably alkoxysilane groups. Such silyl-modified polyurethanes are moisture curable and have been used, for example, as one-component (1K) binder in coatings, adhesives or sealants.

One-component sealants may be prepared by various means. For example, silane-terminated prepolymers may be converted into siloxanes after hydrolysis under moisture. A known system is the MS-Polymer by Kaneka which is based on a silane-terminated polyether, as described, for example, in U.S. Pat. No. 3,971,751.

Another class of sealants are silane-modified polyurethanes, so-called SPUR (Silane-PUR Hybrids), which have become increasingly attractive to manufacturers of adhesives, sealants and coatings. Said high performance hybrid technology is a result of the synergy between the silane-curing mechanism and the polyurethane backbone properties, i.e., good mechanical and performance properties. Formulations based on silane-terminated polyurethanes allow, for example, fast cure at room temperature, good durability, curing with only minimum of gas evolving and a greater variety of additives and adhesion promotors.

According to U.S. Pat. No. 3,632,557 silicon-terminated polyurethanes are obtained by reacting an isocyanate-terminated prepolymer with an aminosilane. Such polymers tend to have high viscosities due to the presence of urea groups.

U.S. Pat. Nos. 4,625,012 and 6,355,127 B1 disclose the use of isocyanato-organosilanes to obtain silyl-modified polyurethanes. Likewise, such polymers tend to have high viscosities and low elongations.

In WO 2012/003187 A1 silicon compounds with a hydrogen-silicon bond and a cross-linkable group are used to modify polyurethanes.

The object of EP 2468791 A1 are epoxy compositions that comprise compounds with five-membered cyclic ring systems comprising oxygen and sulfur, especially 1,3-oxathiolane-2-thione.

D. D. Reynolds, D. L. Fields and D. L. Johnson, Journal of Organic Chemistry, 1961, pages 5111 to 5115, disclose compounds with a five-membered cyclic monothiocarbonate ring system and reactions thereof. Inter alia a reaction with an amino compound is mentioned.

WO 2019/034468 A1 and WO 2019/034469 A1 relate to a process for the synthesis of a compound with at least one monothiocarbonate group.

WO 2019/034470 A1 and WO 2019/034473 A1 relate to polymers which are obtained by reacting compounds with at least one monothiocarbonate group.

Using structural units based on polyethers as a soft segment in sealants are well-established, for example, as described in U.S. Pat. No. 6,103,850 A.

However, there is still a need for prepolymers having urethane groups and moisture-curable silyl groups, especially polymers having additional heteroatoms or functionalities which improve the technical application of said polymers and/or allow to extend the field of technical applications. Further, there is a need of a process for preparing silyl-modified polyurethanes without using isocyanates to avoid toxicological issues.

SUMMARY OF THE INVENTION

Therefore, it is an object of the present invention to provide a process of preparing a silyl-terminated, urethane group containing prepolymer, which is economic and flexible.

Further, it is an object of the present invention to provide a silyl-terminated, urethane group containing prepolymer which is stable under anhydrous conditions and allows fast curing at room temperature when exposed to moisture, suitable for a variety of technical applications.

Further, it is an object of the present invention to provide a silyl-modified, urethane group containing polymer suitable to be used for a variety of technical applications.

Further, it is an object of the present invention to provide a process of preparing a silyl-modified, urethane group containing polymer, which is economic and flexible.

It has now been found that using a cyclic thiocarbonate offers a unique and cost-effective access to polymer hybrids comprising urethane units and thioether units or disulfide units combined with silane functionalities. Such prepolymers are especially suitable for use in one-component sealant or adhesive compositions having improved properties like increased chemical stability, increased refractive index and transparency.

Accordingly, in a first aspect the invention relates to a process for preparing a prepolymer comprising a urethane group and a curable silicon-functional group, which process comprises a) a compound A) with at least one five-membered cyclic monothiocarbonate group and a compound B) with at least one amino group, selected from primary or secondary amino groups or blocked primary or secondary amino groups, and optionally a compound C) with at least one functional group that reacts with a group —SH, are used as starting materials, wherein at least one of the compounds used as starting material comprises a silicon-functional group, and wherein compounds A), B) and optionally C) are processed by b) reacting compounds A) and B) and optionally C) under exclusion of water to obtain a prepolymer with a silicon-functional group that is curable.

In a further aspect, the invention relates to a prepolymer comprising a urethane group and a curable silicon-functional group, obtainable by the process steps a) and b), as defined in any aspect herein.

In a further aspect, the invention relates to a prepolymer comprising (a) a group of formula

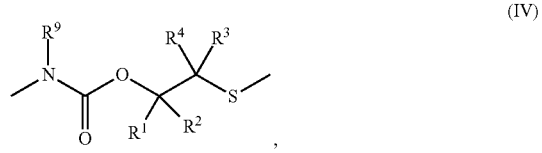

(IV)

and (b) a curable silicon-functional group.

In a further aspect, the invention relates to a composition, especially a one-component sealant or adhesive composition, comprising a prepolymer, as defined in any aspect herein.

In a further aspect, the invention relates to the use of the prepolymer, as defined in any aspect herein, as a component of a composition, preferably of a one-component sealant or adhesive composition.

In a further aspect, the invention relates to a cross-linked polymer comprising monomer units derived from compound A), compound B) and optionally compound C), wherein the polymer comprises 0.001 to 0.3 mol of silicon per 100 g of the cross-linked polymer, as defined in any aspect herein.

In a further aspect, the invention relates to a process for preparing a cross-linked polymer comprising a urethane group and a siloxane linkage, which process comprises step a) and b), as described; and step b2) applying the prepolymer obtained in b) to a surface, gap or a three-dimensional template and curing the silicon-functional group with ambient water.

In a further aspect, the invention relates to a cross-linked polymer obtainable by the process steps a), b) and b2), as defined in any aspect herein.

BRIEF DESCRIPTION OF THE DRAWING

The FIGURE shows a graph of the transmission spectrum between 200 and 1000 nm of 2 glass plates and Example 8 between 2 glass plates.

DETAILED DESCRIPTION OF THE INVENTION

The term "polymer hybrid", as used herein, means a polymer having both a cured inorganic network and a cured organic network.

The term "one-component sealant composition", as used herein, means a composition containing a prepolymer which have curable groups, intended to be applied on a surface/substrate.

The term "one-component adhesive composition", as used herein, means a composition containing a prepolymer which have curable groups, intended to be applied between two substrates.

The term "sealant", as used herein, means a composition containing a cross-linked polymer, finally applied on a surface/substrate.

The term "adhesive", as used herein, means a composition containing a cross-linked polymer, finally applied between two substrates.

As used herein, the singular forms of the articles "a", "an" and "the" include plural forms unless the content clearly dictates otherwise.

The FIGURE is a graph showing the transmission spectrum between 200 and 1000 nm (dashed line: Example 8 between 2 glass plates, continuous line: 2 glass plates as comparison).

The instant process for preparing a prepolymer comprising a urethane group and a curable silicon-functional group are made by compound A), compound B) and optionally compound C). Generally, the prepolymers comprise a S-functional group, especially a thioether group and/or a disulfide group.

The instant process may also provide a composition comprising one or more prepolymers comprising a urethane group and a curable silicon-functional group.

Accordingly, in a further aspect the invention relates to a process for preparing a composition comprising one or more prepolymers comprising a urethane group and a curable silicon-functional group, which process comprises a) a compound A) with at least one five-membered cyclic monothiocarbonate group and a compound B) with at least one amino group, selected from primary or secondary amino groups or blocked primary or secondary amino groups, and optionally a compound C) with at least one functional group that reacts with a group —SH, are used as starting materials, wherein at least one of the compounds used as starting material comprises a silicon-functional group, and wherein compounds A), B) and optionally C) are processed by b) reacting compounds A) and B) and optionally C) under exclusion of water to obtain a composition comprising one or more prepolymers with a silicon-functional group that is curable.

Compound A) comprises at least one five-membered cyclic monothiocarbonate group.

The five-membered cyclic monothiocarbonate group is a ring system with 5 members, three of them are from the monothiocarbonate —O—C(=O)—S—, and the further two members are carbon atoms closing the five-membered cycle.

Compound A) may be a low molecular compound or a polymeric compound and may comprise, for example, up to 1000, notably up to 500, preferably up to 100 five-membered cyclic monothiocarbonate groups.

In a preferred embodiment, compound A) comprises one to three cyclic monothiocarbonate groups.

In a most preferred embodiment, compound A) comprises one or two five-membered cyclic monothiocarbonate groups.

Preferred compounds A) have a molecular weight of up to 10000 g/mol, notably up to 5000 g/mol and particularly up to 1000 g/mol. Most preferred are compounds A) having a molecular weight of up to 500 g/mol.

Compounds A) may comprise other functional groups, for example, non-aromatic, ethylenically unsaturated groups, ether groups, thioether groups or carboxylic ester groups or a silicon-functional group.

In a preferred embodiment, compounds A) do not comprise other functional groups than cyclic monothiocarbonate groups, non-aromatic, ethylenically unsaturated groups, ether groups, thioether groups, carboxylic ester groups or silicon-functional groups.

Preferred compounds A) are compounds of formula (I) and/or of formula (II).

A preferred compound A) is a compound of formula

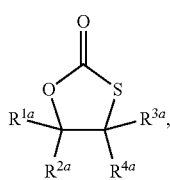

(I)

wherein
$R^{1a}$ to $R^{4a}$ independently from one another are hydrogen or an organic group with up to 50 carbon atoms,
wherein, alternatively, $R^{2a}$, $R^{4a}$ and the two carbon atoms of the thiocarbonate group may also together form a five to ten membered carbon ring,
or a compound of formula

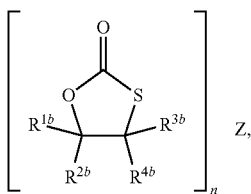

(II)

wherein
$R^{1b}$ to $R^{4b}$ independently from one another are hydrogen or an organic group with up to 50 carbon atoms,
wherein, alternatively, $R^{2b}$, $R^{4b}$ and the two carbon atoms of the monothiocarbonate group may also together form a five to ten membered carbon ring;
one of the groups $R^{1b}$ to $R^{4b}$ is a linking group to Z,
n is an integral number of at least 2, and
Z is a n-valent organic group.

Compounds A) of formula (I) have one five-membered cyclic monothiocarbonate group, only.

In case that any of $R^{1a}$ to $R^{4a}$ is an organic group, such organic group is preferably an organic group with up to 30, more preferably up to 20 carbon atoms.

In a further preferred embodiment, $R^{2a}$ and $R^{4a}$ do not form a five to ten membered carbon ring together with the two carbon atoms of the thiocarbonate group.

In case that any of $R^{1a}$ to $R^{4a}$ is an organic group, such organic group may comprise heteroatoms and functional groups. Examples of functional groups are, for example, a non-aromatic, ethylenically unsaturated group, an ether group, a thioether group, a carboxylic ester group or a silicon-functional group. As suitable heteroatoms the organic group may comprise O, N, S, Si and/or Cl. $R^{1a}$ to $R^{4a}$ may comprise oxygen, for example, in form of an ether group, a hydroxy group, an aldehyde group, a keto group or a carboxy group. In a preferred embodiment, the organic group is an aliphatic organic group with up to 30 carbon atoms which may comprise O, N or Cl, in particular oxygen.

The reacted compounds A) within the prepolymer or the composition comprising the prepolymer should be compatible with the curable silicon-functional groups, i.e., stable under anhydrous conditions.

In a more preferred embodiment, the organic group is selected from an alkyl group, from a group —$CH_2$—O—$R^{5a}$ or a group —$CH_2$—O—$C(=O)$—$R^{6a}$ or a group —$CH_2$—$NR^{7a}R^{8a}$, wherein $R^{5a}$ to $R^{8a}$ are an organic group with up to 30 carbon atoms, preferably up to 20 carbon atoms. In particular, $R^{5a}$ to $R^{8a}$ are an aliphatic or aromatic group, which may comprise oxygen, for example, in form of ether groups. In a preferred embodiment, $R^{5a}$ to $R^{8a}$ are an aliphatic hydrocarbon group, such as an alkyl group with 1 to 10 carbon atoms, an alkoxy group or a polyalkyleneoxy group. In a most preferred embodiment, $R^{5a}$ to $R^{8a}$ are an aliphatic hydrocarbon group, notably an alkyl group with 1 to 10 carbon atoms.

In a most preferred embodiment, the organic group is an alkyl group, a group —$CH_2$—O—$R^{5a}$ or a group —$CH_2$—O—$C(=O)$—$R^{6a}$, wherein $R^{5a}$ and $R^{6a}$ are an alkyl group with 1 to 10 carbon atoms.

Preferably, two to all four of $R^{1a}$ to $R^{4a}$ in formula (I) are H, and the remaining groups $R^{1a}$ to $R^{4a}$ are an organic group.

More preferably, two or three of $R^{1a}$ to $R^{4a}$ in formula (I) are H, and the remaining groups $R^{1a}$ to $R^{4a}$ are an organic group, especially an alkyl group, a group —$CH_2$—O—$R^{5a}$ or a group —$CH_2$—O—$C(=O)$—$R^{6a}$.

Most preferably, three of $R^{1a}$ to $R^{4a}$ in formula (I) are H, and the remaining group of $R^{1a}$ to $R^{4a}$ is an organic group. In a preferred embodiment, $R^{1a}$ or $R^{2a}$ is the remaining group representing an organic group, especially an alkyl group, a group —$CH_2$—O—$R^{5a}$ or a group —$CH_2$—O—$C(=O)$—$R^{6a}$.

As preferred compounds A) with one five-membered cyclic monothiocarbonate group may be mentioned, for example, compounds A) of formulae

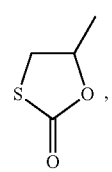

(Ia)

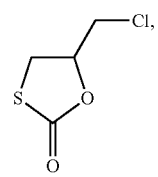

(Ib)

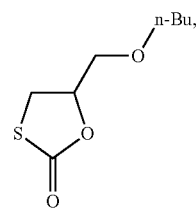

(Ic)

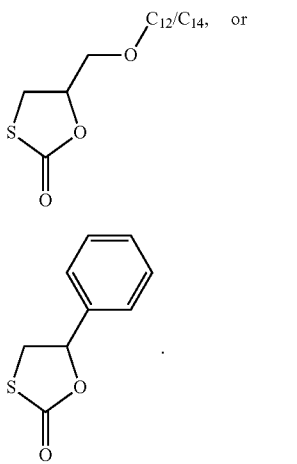

The substituent "C$_{12/14}$" means a substituent derived from C$_{12}$/C$_{14}$ fatty alcohol.

Compounds A) of formula (II) have at least two five-membered cyclic monothiocarbonate groups.

In case that any of R$^{1b}$ to R$^{4b}$ is an organic group, such organic group is preferably an organic group with up to 30 carbon atoms. In a further preferred embodiment R$^{2b}$ and R$^{4b}$ do not form a five to ten membered carbon ring together with the two carbon atoms of the thiocarbonate group.

In case that any of R$^{1b}$ to R$^{4b}$ is an organic group, such organic group may comprise other elements than carbon and hydrogen. In particular, it may comprise O, N, S, Si or Cl. In a preferred embodiment, the organic group may comprise O or Cl. R$^{1b}$ to R$^{4b}$ may comprise oxygen, for example, in form of an ether group, a hydroxy group, an aldehyde group, a keto group or a carboxy group.

The reacted compounds A) within the prepolymer or the composition comprising the prepolymer should be compatible with the curable silicon-functional groups, i.e., stable under anhydrous conditions.

One of the groups R$^{1b}$ to R$^{4b}$ is the linking group to Z.

Preferably, the linking group is a single bond or a group selected from —CH$_2$—, —CH$_2$—O—, —CH$_2$O—C(=O)— or —CH$_2$—NR$^{5b}$—, wherein R$^{5b}$ is an aliphatic group, notably an alkyl group with at maximum 20 carbon atoms.

More preferably, the linking group is a single bond or a group selected from —CH$_2$—, —CH$_2$O— or —CH$_2$O—C(=O)—. In a most preferred embodiment, the linking group is a group —CH$_2$O—.

Preferably, two or three of the groups R$^{1b}$ to R$^{4b}$ in formula (II) are H.

In a most preferred embodiment three of the groups R$^{1b}$ to R$^{4b}$ represent H, and the remaining group of R$^{1b}$ to R$^{4b}$ is the linking group to Z.

In a most preferred embodiment groups R$^{1b}$ or R$^{2b}$ is the linking group to Z.

n is an integral number of at least 2. For example, n may be an integral number from 2 to 1000, specifically from 2 to 100, in particular 2 to 10.

In a preferred embodiment n is an integral number from 2 to 5, in particular n is 2 or 3.

In a more preferred embodiment n is 2.

Z is a n-valent organic group. In case of a high number of n, such as, for example, 10 to 1000, Z may be a polymeric group, in particular a polymer-backbone, obtained, for example, by polymerization or copolymerization, such as radical polymerization of ethylenically unsaturated monomers, polycondensation or polyaddition. For example, polyesters or polyamides are obtained via polycondensation under elimination of water or alcohol and polyurethanes or polyureas are obtained via polyaddition.

Such compounds of formula (II) are, for example, polymers obtained by radical polymerization or copolymerization of ethylenically unsaturated monomers comprising monothiocarbonate groups or of monomers comprising epoxy groups which are then transferred into a monothiocarbonate group.

In a preferred embodiment Z is a n-valent organic group with up to 50 carbon atoms, in particular up to 30 carbon atoms, and which may comprise other elements than carbon and hydrogen, and n is an integral number from 2 to 5, notably 2 or 3, most preferred 2.

In a particularly preferred embodiment Z is a n-valent organic group with up to 50 carbon atoms, in particular up to 30 carbon atoms, and which comprises carbon, hydrogen and optionally oxygen, only and no further elements and n is an integral number from 2 to 5, notably 2 or 3, most preferred 2.

In a preferred embodiment Z is a polyalkoxylene group of formula $$(V-O-)_mV \quad (G1),$$ wherein V is a C$_2$-C$_{20}$-alkylene group, and m is an integral number of at least 1. The terminal alkylene groups V are bonded to the linking group, which is one of the groups R$^{1b}$ to R$^{4b}$.

Preferably, the C$_2$-C$_{20}$-alkylene group is a C$_2$-C$_4$-alkylene group, in particular ethylene or propylene. m may, for example, be an integral number from 1 to 100, in particular from 1 to 50.

In a further preferred embodiment Z is a divalent group of formula

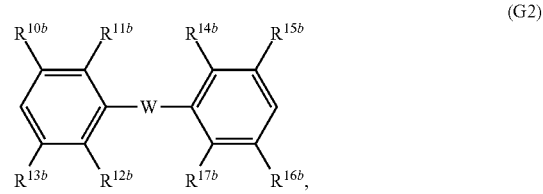

wherein

W is a bivalent organic group with at maximum 10 carbon atoms, and n is 2 (within formula (II)), and R$^{10b}$ to R$^{17b}$ independently from one another are H or a C$_1$-C$_4$-alkyl group, and wherein the two hydrogen atoms in the para-position to W are replaced by the bond to the linking group, which is one of the groups R$^{1b}$ to R$^{4b}$.

Preferably, at least six of R$^{10b}$ to R$^{17b}$ are H. In a most preferred embodiment all of R$^{10b}$ to R$^{17b}$ are H.

Groups W are, for example: —CH$_2$—, —CH(CH$_3$)—, —C(CH$_3$)$_2$—, —C(CH$_3$)(C$_2$H$_5$)— or —SO$_2$—.

Preferably, W is an organic group that consists of carbon and hydrogen, only.

Most preferred W is C(CH$_3$)$_2$, which corresponds to the structure of bisphenol A.

In a further preferred embodiment Z is a group G3, wherein G3 is an alkylene group, notably a C$_2$-C$_8$-alkylene group; preferred examples of such an alkylene group are ethylene (CH$_2$—CH$_2$), n-propylene (CH$_2$—CH$_2$—CH$_2$) and notably n-butylene (CH$_2$—CH$_2$—CH$_2$—CH$_2$).

Compounds A) with at least two five-membered cyclic monothiocarbonate groups are, for example, compounds of formula

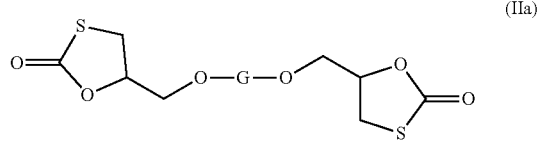

(IIa)

wherein G represents an alkylene group with 2 to 10, notably 2 to 6 carbon atoms.

A preferred compound of formula (IIa) is bis-1,3-oxathiolane-2-one-5,5'-[1,4-butanediylbis(oxymethylene)] which has the formula

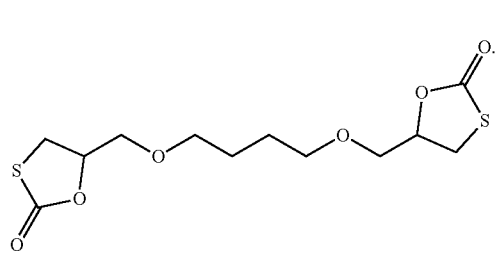

(IIb)

Compound A) may be a mixture of different compounds A).

A mixture of different compounds A) may be one or more compounds of formula (I), preferably 1 or 2 compounds of formula (I), especially of formula (Ia) to (Ie), or a mixture of a compound A) of formula (I) and a compound A) of formula (II), for example, of formula (IIa), especially of formula (IIb).

Further preferred is a mixture of compounds A) of formula (I), wherein three of $R^{1a}$ to $R^{4a}$ in formula (I) are hydrogen, and the remaining group of $R^{1a}$ to $R^{4a}$ is an organic group, and $R^{1a}$ or $R^{2a}$ is the remaining group representing an organic group, especially an alkyl group, a group —$CH_2$—O—$R^{5a}$ or a group —$CH_2$O—C(=O)—$R^{6a}$, wherein $R^{5a}$ and $R^{6a}$ are an alkyl group with 1 to 10 carbon atoms.

Further preferred is a mixture of a compound A) of formula (I) and a compound A) of formula (II), for example, of formula (IIa), especially of formula (IIb), which may be present in amount of up to 30 wt %, based on the total weight of compounds A), preferably up to 20 wt %.

More preferably, a mixture of compounds A) of formula (I) is used, especially a mixture of compounds A) of formula (Ia) to (Ie), in particular a mixture of compounds of formula (Ia) to (Ic).

Compound A), respectively the mixture of compounds A), is liquid at 21° C., 1 bar. In one preferred embodiment the liquid compound A) is obtained by solving a compound A) which is solid at 21° C., 1 bar in a compound A) which is liquid at 21° C., 1 bar.

In a preferred embodiment, compound A) is liquid at 21° C., 1 bar.

Some methods for the synthesis of compounds A) with one monothiocarbonate group are described in the state of the art.

According to U.S. Pat. Nos. 3,072,676 and 3,201,416 ethylene monothiocarbonates may be prepared by a two-step-process. In a first step mercaptoethanol and chlorocarboxylates are reacted to give hydroxyethylthiocarbonate, which is heated in the second step in a presence of metal salt catalyst to the ethylene monothiocarbonate.

According U.S. Pat. No. 3,517,029 alkylene monothiocarbonates are obtained by reacting mercaptoethanol and a carbonate diester in the presence of a catalytically active salt of thorium.

According to the process disclosed in U.S. Pat. No. 3,349,100 alkylene monothiocarbonates are obtained by reacting an epoxide with carbonyl sulfide. The availability of carbonyl sulfide is limited. Yields and selectivities of alkylene monothiocarbonates obtained are low.

A synthesis using phosgene as starting material is known from U.S. Pat. No. 2,828,318. Phosgene is reacted with hydroxymercaptanes. Yields of monothiocarbonates are still low and by products from polymerization are observed.

A preferred process for the preparation of compounds A) and C), is a process wherein a) a compound with at least one epoxy group (shortly referred to as epoxy compound) is used as starting material, b) the compound is reacted with phosgene or an alkyl chloroformate thus giving an adduct, and c) the adduct is reacted with a compound comprising anionic sulfur to give the compound with at least one five-membered cyclic monothiocarbonate groups This process is in detail described in WO 2019/034469 A1.

Compound B) is a compound with at least one amino group, selected from a primary or a secondary amino group or a blocked primary or secondary group. As used herein, the term "amino group" means a primary or secondary amino group if not indicated otherwise or obvious from the content otherwise.

Compounds B) do not comprise any monothiocarbonate groups.

Compound B) may have, for example, a molecular weight of up to 500,000 g/mol. The latter might be the case if compound B) is a high molecular compound such as a polymer comprising amino groups.

In case of a polymer the term "molecular weight", as used herein, means the number average molecular weight Mn, as usually determined by gel-permeation chromatography (GPC) against polystyrene as standard.

Compound B) may be an adduct, for example, an urethane groups-comprising adduct obtained by reacting compounds with cyclic monothiocarbonate groups and compounds with primary or secondary amino groups, wherein the amino groups are in stoichiometric excess compared to the monothiocarbonate groups, thus giving a urethane groups-comprising adduct which still has primary or secondary amino groups, but essentially no monothiocarbonate groups.

Preferred compounds B) have a molecular weight of up to 10000 g/mol, notably of up to 5000 g/mol and particularly of up to 1000 g/mol. Most preferred are compounds B) having a molecular weight of from 60 g/mol to 500 g/mol.

Compounds B) may comprise, for example, polymerizable, ethylenically unsaturated groups, ether or carboxylic ester groups or silicon-functional groups.

In a preferred embodiment compounds B) do not comprise any other functional groups than primary or secondary amino groups, tertiary amino groups, polymerizable, ethylenically unsaturated groups, ether groups or silicon-functional groups.

In a preferred embodiment compounds B) comprise 1 to 10 amino groups, preferably 1 to 5, respectively 1 to 3 amino groups and, in a most preferred embodiment, compound B) comprises 1 to 2 amino groups.

In a preferred embodiment at least one of the amino groups of compound B) is a primary amino group.

In a most preferred embodiment, all amino groups of compound B) are primary amino groups.

Compounds B) with one amino group are, for example, monoalkylamines with a primary amino group such as $C_1$-$C_{20}$-alkylamines or cycloalkyl amines or etheramines such as 2-methoxyethylamine or 3-methoxypropylamine or di- or polyether amines such as di- or polyglycol amine, polyoxypropylene amine.

Compounds B) with more than one amino group are, for example,

- alkylene-diamines or alkylene-polyamines such as ethylene diamine, propylene diamine, butylene diamine, pentamethylene diamine, hexamethylene diamine, neopentane diamine, octamethylene diamine, 1,3-diaminopentane, 2-methylpentane-1,5-diamine; or 1,1,1-tris(aminomethyl)ethane;
- alkylene-diamines or alkylene-polyamines comprising ether groups (polyetheramines) such as polyglycol diamine or polyoxypropylene diamine;
- cycloaliphatic diamines, such as cyclohexyldiamines, for example, 1,2-diaminocyclohexane, 1-methyl-2,4-diaminocyclohexane, 1-methyl-2,6-diaminocyclohexane or mixtures thereof, isophorone diamine, bis(4-aminocyclohexyl)methane, 1,3-bis(aminomethyl)cyclohexane, 1,4-bis(aminomethyl)cyclohexane, 2,5-bisaminomethyl-tetrahydrofuran, or 3,3'-dimethyl-4,4'diamino-dicyclohexylmethane;
- aromatic diamines, such as 1,2-phenylendiamine or 1,4 phenylendiamine, toluene diamines, 4,4' diamino-diphenylmethane, 4,4' diaminodiphenylsulfone, 2,5-bisaminomethyl-furan.

Compounds B) may also be used in a form, wherein the amino groups are protected with a protecting group. As soon as it become necessary or desired the protecting group is removed so that the compounds B) above with free amino groups are obtained. Usually, removal of the protecting groups occurs under the conditions of the reaction. Usual protected amino groups for amino groups are, for example, ketimines, aldimines, imidazolidines, oxazolidines, lewis acid complexed amines, carbamates, benzyloxycarbonyl amines, acyloximes, or formanilides. The deprotecting reaction can, for example, be triggered by either temperature, light, pH or the presence of water/humidity.

Further suitable compounds B) are, for example, listed in WO 2019/034470 A1 and WO 2019/034473 A1.

Compound B) may be a mixture of different compounds B).

Compounds C) are compounds with at least one functional group that reacts with a thiol group —SH.

Compounds C) do not comprise five-membered cyclic monothiocarbonate groups and do not comprise amino groups.

Compounds C) may have, for example, a molecular weight of up to 500,000 g/mol. The latter might be the case if compound C) is a high molecular compound such as a polymer.

Preferred compounds C) have a molecular weight of up to 10000 g/mol, notably of up to 5000 g/mol and particularly of up to 1000 g/mol. Most preferred are compounds C) having a molecular weight of from 60 g/mol to 500 g/mol.

Compounds C) may have, for example, up to 1000 functional groups that react with a group —SH, notably up to 500 and preferably up to 100 functional groups that react with a group —SH.

In a preferred embodiment compound C) comprises 1 to 10, notably 2 to 6 functional groups that react with a group —SH.

In a most preferred embodiment compound C) comprises 2 or 3 functional groups that react with a group —SH.

In a preferred embodiment, the reaction of the functional group of compound C) with the group —SH results in the formation of a sulfur-carbon bond.

The reaction of the functional group of compound C) with the group —SH may be an addition reaction, a condensation reaction or a nucleophilic substitution reaction.

Compounds C), that undergo an addition reaction with the group —SH, are, for example, compounds with non-aromatic, ethylenically unsaturated groups or compounds with epoxy groups or compounds with isocyanate groups as functional groups. Non-aromatic, ethylenically unsaturated groups are non-aromatic carbon-carbon double bonds or carbon-carbon triple bonds.

Compounds C), that undergo a condensation reaction with the group —SH are, for example, compounds with carbonyl groups as functional group, for example mono carbonyl compounds or dicarbonyl compounds such as dialdehydes or diketones.

Compounds C), that undergo a nucleophilic substitution reaction with the group —SH are, for example, compounds with an halogenide, notably chloride, as functional group.

The term «halogenide», as used herein, is the trivial name of a covalently bonded halogen atom, preferably a Cl atom. The term "chloride", as used herein, is the trivial name of a covalently bonded Cl atom.

Preferred functional groups that react with a group —SH are non-aromatic, ethylenically unsaturated groups or epoxy groups, more preferably non-aromatic, ethylenically unsaturated groups.

Preferred examples of a polymerizable, ethylenically unsaturated group are the vinyl group $H_2C\!\!=\!\!CH\!\!-\!\!$, the ethinyl group $HC\!\!\equiv\!\!C\!\!-\!\!$, an olefinic group $-\!\!HC\!\!=\!\!CH\!\!-\!\!$, wherein the two carbon atoms of the double bond are each substituted by one hydrogen, only, and the further substituents are notably carbon atoms, including carbon atoms of a cyclic system, the group $-\!\!C\!\!\equiv\!\!C\!\!-\!\!$, and the acrylic or methacrylic group, shortly referred to as (meth)acrylic group. As used herein, the term "vinyl group" does not include the (meth)acrylic group.

More preferred compounds C) are compounds with vinyl groups, (meth)acrylic groups or epoxy groups, most preferably vinyl groups, ethinyl groups or (meth)acrylic groups, especially (meth)acrylic groups, in particular methacrylic groups.

The reacted compounds C) within the prepolymer or the composition comprising the prepolymer should be compatible with the curable silicon-functional groups, i.e., stable under anhydrous conditions.

Compounds with vinyl groups, (meth)acrylic groups or epoxy groups are well known.

Suitable compounds C) are listed, for example, in WO 2019/034470 A1 and WO 2019/034473 A1.

Compound C) may be an adduct, for example, a urethane groups-containing adduct obtained by reacting a hydroxy-substituted (meth)acrylic ester with an alkylene-diisocyanate, thus giving a urethane groups-containing adduct having terminal (meth)acrylate groups. A suitable compound is, for example, diurethane dimethacrylate. Also adducts are available by reacting hydroxy-substituted vinyl compounds.

Compound C) may be a mixture of different compounds C).

At least one of the compounds reacted comprises a silicon-functional group.

In case that compounds A) and B) are reacted, at least one of compounds A) or B) comprises a silicon-functional group.

In case that compounds A), B) and C) are reacted, at least one of compounds A), B) or C) comprises a silicon-functional group.

More than one compound of A) and B), respectively A), B) and C) may comprise a silicon-functional group. Preferably, only one of the compounds reacted is a compound comprising a silicon-functional group.

As mentioned herein-before, compounds A), B) and C) may be mixtures of different compounds A), B) and C). Hence, the desired content of silicon-functional groups in the polymer obtained from compounds A), B) and optionally C) can easily be obtained by using mixtures of compounds with silicon-functional groups and without silicon-functional groups.

In a preferred embodiment compound B) or compound C) comprise a silicon-functional group.

The silicon-functional group is preferably a group with at least one silicon atom and at least one group that is cross-linkable through a silanol cross-linking reaction.

The silicon-functional group may comprise more than one silicon atom. The silicon atoms may be bonded to each other directly or via an oxygen bridge. In a preferred embodiment, the silicon-functional group comprises 1 to 3 silicon atoms. Most preferred are silicon-functional groups with only one silicon atom.

Groups that are cross-linkable through a silanol cross-linking reaction are preferably the hydroxy group and hydrolysable groups, notably alkoxy groups; alkoxy groups are preferred, notably $C_1$-$C_{10}$-alkoxy groups.

The silicon-functional group may comprise more than one group which is cross-linkable through a silanol cross-linking reaction. The possible number of groups which are cross-linkable through a silanol cross-linking reaction depends on the number of silicon atoms in the silicon-functional group.

The silicon-functional groups may, in addition, comprise hydrogen, alkyl or alkylene-vinyl groups that are bonded to the silicon atoms. In a preferred embodiment, the silicon-functional groups may comprise alkyl or alkylene-vinyl groups but does not comprise hydrogen that is bonded to the silicon atoms.

Preferably, the silicon-functional groups do not comprise any other constituents than silicon, groups which are cross-linkable through a silanol cross-linking reaction, hydrogen, alkyl or alkylene-vinyl groups that are all bonded to silicon and oxygen as possible bridge between silicon atoms.

More preferably, the silicon-functional group is an alkoxysilane group of formula —SiR$^{1s}$R$^{2s}$R$^{3s}$ (III), wherein at least one of the groups R$^{1s}$ to R$^{3s}$ is an alkoxy group and the other groups R$^{1a}$ to R$^{3s}$ are hydrogen, an alkyl group or an alkylene-vinyl group.

Most preferably, the silicon-functional group is an alkoxysilane group of formula —SiR$^{1s}$R$^{2s}$R$^{3s}$ (III), wherein at least one of the groups R$^{1s}$ to R$^{3s}$ is an alkoxy group and the other groups R$^{1s}$ to R$^{3s}$ are an alkyl group or an alkylene-vinyl group, especially one alkyl group.

The alkoxy group is preferably a $C_1$-$C_{10}$-alkoxy group, notably a $C_1$-$C_4$-alkoxy group, for example, a butoxy, propoxy, ethoxy or methoxy group. Most preferably, the alkoxy group is an ethoxy or methoxy group.

The alkyl group is preferably a $C_1$-$C_{10}$-alkyl group, notably a $C_1$-$C_4$-alkyl group, for example, a butyl, n-propyl, ethyl or methyl group. Most preferably, the alkyl group is an ethyl or methyl group.

The alkylene-vinyl group is preferably a $C_2$-$C_8$-alkylene-vinyl group, notably a $C_1$-$C_2$-alkylene-vinyl group, more preferably a vinyl or allyl group.

Preferably, two or three of the groups R$^{1s}$ to R$^{3s}$ are an alkoxy group, and the remaining groups R$^{1s}$ to R$^{3s}$ are hydrogen, an alkyl group or an alkylene-vinyl group.

More preferably, two or three of the groups R$^{1s}$ to R$^{3s}$ are an alkoxy group and any remaining group R$^{1s}$ to R$^{3s}$ is an alkyl group or alkylene-vinyl group. For example, two or three of the groups R$^{1s}$ to R$^{3s}$ are methoxy or ethoxy, and any remaining group R$^{1s}$ to R$^{3s}$ is methyl, ethyl, vinyl or allyl.

Most preferably, two of the groups R$^{1s}$ to R$^{3s}$ are an alkoxy group and any remaining group R$^{1s}$ to R$^{3s}$ is an alkyl group or alkylene-vinyl group, preferably an alkyl group.

Preferred compounds A) with a silicon-functional group comprise one or two five-membered cyclic monothiocarbonate groups, particularly one five-membered cyclic monothiocarbonate group, and one alkoxysilane group —SiR$^{1s}$R$^{2s}$R$^{3s}$.

Particularly preferred compounds are compounds of formula (VII)

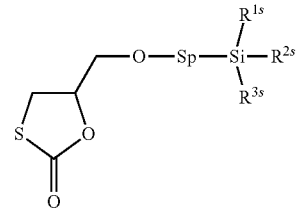

wherein R$^{1s}$ to R$^{3s}$ have the meaning above, and Sp is a spacer group, which is an organic group with 1 to 20, notably 1 to 10, preferably 1 to 6, notably 1 to 3 carbon atoms. Sp may comprise other atoms than carbon and hydrogen, for example, nitrogen, oxygen or sulfur. Preferably, Sp is a hydrocarbon group that may comprise oxygen, for example, in form of ether groups, but no other heteroatoms. In a particularly preferred embodiment, Sp is an alkylene group with 1 to 20, notably 1 to 10 and most preferably 1 to 6, notably 1 to 3 carbon atoms.

A specific example of a compound of formula (VIIa) is the compound below:

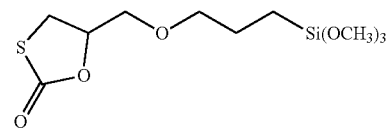

Compounds of formula (VII) may be prepared in accordance with the process as described in WO 2019/024469 A1.

Preferred compounds B) with a silicon-functional group comprise one or two amino groups, particularly one amino group, and one alkoxysilane group —SiR$^{1s}$R$^{2s}$R$^{3s}$.

Suitable examples of compound B) with a silicon-functional group is 3-aminopropyldimethoxymethylsilane, 3-aminopropyltrimethoxysilane, 3-(N,N-dimethylaminopropyl)-aminopropylmethyldimethoxysilane or 3-(N,N-dimethylaminopropyl)aminopropyltrimethoxysilane.

Preferred compounds C) with a silicon-functional group comprise one or two functional groups, that react with a group —SH, and one alkoxysilane group —SiR$^{1s}$R$^{2s}$R$^{3s}$.

Suitable examples of compounds C) with a silicon-functional group are 3-trimethoxysilylpropyl methacrylate, 3-(dimethoxymethylsilyl)propyl methacrylate, trimethoxysilylpropyl acrylate or 3-(dimethoxymethylsilyl)propyl acrylate, preferably trimethoxysilylpropyl methacrylate or 3-(dimethoxymethylsilyl)propyl methacrylate.

Further suitable is a compound C) with a silicon-functional group of formula

  —SiR$^{1s}$R$^{2s}$R$^{3}$  (III), wherein two of the groups R$^{1s}$ to R$^{3s}$ are an alkoxy group, and the remaining group of R$^{1s}$ to R$^{3s}$ is an alkylene-vinyl group, especially a vinyl or allyl group.

Further suitable is a compound C) with a silicon-functional group of formula

  —SiR$^{1s}$R$^{2s}$R$^{3s}$  (III), wherein

R$^{1s}$ is an alkoxy group, R$^{2s}$ is an alkyl group, and R$^{3s}$ is an alkylene-vinyl group, especially a vinyl or allyl group.

A trimethoxysilylpropyl glycidylether is a suitable compound C) having an epoxy group and a silicon-functional group, when the reacted compound C) within the prepolymer or the composition comprising the prepolymer should be compatible with the silicon-functional groups, i.e., stable under anhydrous conditions.

At least one of the compounds A), B) or optionally C) may comprise a soft segment.

Preferably, at least one of the compounds A), B) or optionally C) used as starting materials comprises a segment selected from a polyether group or an organic polysulfide group (aliphatic polysulfide group).

Accordingly, in a preferred aspect the invention relates to a process for preparing a prepolymer comprising a urethane group and a curable silicon-functional group, wherein at least one of the compounds A), B) or optionally C) used as starting materials comprises a segment selected from a polyether group or an organic polysulfide group.

The term "organic polysulfide group" or "aliphatic polysulfide group", as used herein, means an aliphatic polysulfide polymer group derived from an aliphatic polysulfide polymer, obtainable by reaction of 2-haloethanol, formaldehyde and sodium polysulfide Na$_2$S$_x$ (x≥2), or by reaction of bishaloethylformal and sodium polysulfide. 2-Haloethanol is usually 2-chloroethanol, and bishaloethylformal is usually bischloroethylformal.

The polyether group or the organic polysulfide group may be comprised in compound A), compound B) and/or compound C), preferably in compound B) and/or compound C), more preferably in compound B).

The polyether group comprises at least two oxyalkylene units.

The polyether group has units of formula

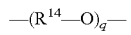  —(R$^{14}$—O)$_q$—  (VIII), wherein

R$^{14}$ is a divalent, straight or branched alkylene group containing 1 to 14 carbon atoms, preferably a straight or branched alkylene group of 2 to 4 carbon atoms, for example, ethylene, propylene or butylene, q is 2 to 70, preferably 2 to 40.

Desirably, the polyether group is based on polyethylene glycol, polypropylene glycol, polyethylene glycol-polypropylene glycol copolymers, polytetramethylene glycol, polytetramethylene glycol-polypropylene glycol copolymers, or polytetramethylene glycol/polypropylene glycol copolymers.

Desirably, the organic polysulfide group comprises an aliphatic polymer group derived from an aliphatic polysulfide polymer, obtainable by reaction of 2-chloroethanol, formaldehyde and sodium polysulfide Na$_2$S$_x$ (x≥2, preferably Na$_2$S$_2$) or by reaction of bischloroethylformal and Na$_2$S$_x$, the polysulfide polymer is represented for x=2 by the general formula

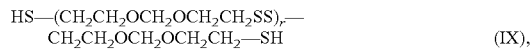

HS—(CH$_2$CH$_2$OCH$_2$OCH$_2$CH$_2$SS)$_r$—
CH$_2$CH$_2$OCH$_2$OCH$_2$CH$_2$—SH  (IX), wherein r is about 4 to 25; the polysulfide polymer has an average molecular weight of about 800 to about 5000 g/mol, and the polysulfide polymer is optionally further cross-linked.

For example, the polymers of formula (IX), optionally cross-linked, are commercially available as Thiokol® polymers.

Thus, a process for preparing a prepolymer comprising a urethane group and a curable silicon-functional group is preferred, wherein at least one of the starting materials comprises a segment of a polyether group having units of formula

  —(R$^{14}$—O)$_q$—  (VIII), wherein

R$^{14}$ is a divalent, straight or branched alkylene group containing 1 to 14 carbon atoms, preferably a straight or branched alkylene group of 2 to 4 carbon atoms, for example, ethylene, propylene or butylene, and q is 2 to 70, preferably 2 to 40; or a segment of an organic polysulfide group comprising an aliphatic polymer group derived from an aliphatic polysulfide polymer, obtainable by reaction of 2-chloroethanol, formaldehyde and Na$_2$S$_2$ or by reaction of bischloroethylformal and Na$_2$S$_2$, the polysulfide polymer is represented by the general formula

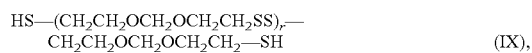

HS—(CH$_2$CH$_2$OCH$_2$OCH$_2$CH$_2$SS)$_r$—
CH$_2$CH$_2$OCH$_2$OCH$_2$CH$_2$—SH  (IX), wherein r is about 4 to 25; the polysulfide polymer has an average molecular weight of about 800 to about 5000 g/mol, and the polysulfide polymer is optionally further cross-linked.

Generally, the polyether group or the organic polysulfide group does not comprise hydroxy or carboxy groups.

Preferably, the prepolymer comprises a segment of a polyether group.

Accordingly, a process for preparing a prepolymer comprising a urethane group and a curable silicon-functional group is preferred, wherein at least one of the starting materials comprises a segment of a polyether group having units of formula

  —(R$^{14}$—O)$_q$—  (VIII), wherein

R$^{14}$ is a divalent, straight or branched alkylene group containing 1 to 14 carbon atoms, preferably a straight or branched alkylene group of 2 to 4 carbon atoms, for example, ethylene, propylene or butylene, and q is 2 to 70, preferably 2 to 40.

A suitable compound A) used as starting material comprising a segment of a polyether group may be a compound A) of formula (II), wherein Z is a polyalkoxylene group of formula $$(V-O-)_m V \qquad (G1),\text{ wherein}$$

V is a $C_2$-$C_4$-alkylene group, and m is an integral number of at least 2. The terminal alkylene groups V are bonded to the linking group, which is one of the groups $R^{1b}$ to $R^{4b}$, as defined herein-before.

Said compounds A) may be prepared in analogy to the process, as described in WO 2019/034469 A1.

Generally, compound A) is only used as starting material comprising a segment of a polyether group.

Accordingly, in a preferred aspect the invention relates to a process for preparing a prepolymer comprising a urethane group and a curable silicon-functional group, wherein at least one of the compounds A), B) or optionally C) used as starting materials comprises a segment selected from a polyether group or an organic polysulfide group, with the proviso that, if compound A) is used as starting material, compound A) does not comprise a segment of an organic polysulfide group.

A suitable compound B) used as starting material comprising a segment of a polyether group may be a compound like an alkylene-diamine or an alkylene-polyamine comprising at least two ether groups.

An alkylene-diamine or an alkylene-polyamine comprising at least two ether groups are polyoxyalkyleneamines (polyetheramines). Said polyoxyalkyleneamines are, for example, based on polyethylene glycol, polypropylene glycol, polypropylene glycol/polyethylene glycol copolymers, polytetramethylene glycol, polytetramethylene glycol/polypropylene glycol copolymers, or polytetramethylene glycol/polypropylene glycol copolymers.

Suitable polyoxyalkylene diamines may be defined by formula $$H_2N-R^{15}-O-(R^{16}-O)_s-R^{17}-NH_2 \qquad (X),\text{ wherein}$$

$R^{15}$, $R^{16}$ and $R^{17}$ independently of one another and in each occurrence $C_2$-$C_4$-alkylene, and s may be from 1 to 70, preferably 1 to 40.

Preferably, $R^{15}$ to $R^{17}$ are the same $C_2$-$C_4$-alkylene, or $R^{15}$ and $R^{17}$ are the same, and $R^{16}$ may be $C_2$-$C_4$-alkylene which is different from $R^{15}$ and $R^{17}$.

$C_2$-$C_4$-alkylene is ethylene, propylene or butylene.

Accordingly, in a preferred aspect, compound B) used as starting material comprising a polyether group is a polyoxyalkylene diamine of formula $$H_2N-R^{15}-O-(R^{16}-O)_s-R^{17}-NH_2 \qquad (X),\text{ wherein}$$

$R^{15}$, $R^{16}$ and $R^{17}$ independently of one another and in each occurrence $C_2$-$C_4$-alkylene, and s may be from 1 to 70, preferably 1 to 40.

Suitable polyoxyalkyleneamines are commercially available under the trade name Jeffamine®, for example, Jeffamine D-230, D-400, D-2000, D-4000, EXTJ-502, EXTJ-511, THF-100 or THF-170 (available from Huntsman). Further commercially available polyoxyalkyleneamines are such as Polyetheramine D 230, D 400, D 403, D 2000 (available from BASF).

The polyoxalkyleneamine may be a polyoxyalkylene triamine, and may be ethylene oxide, propylene oxide or butylene oxide based, or mixtures thereof, and may be prepared by reaction thereof with a triol initiator, e.g., glycerol, trimethylolpropane, trimethylolethane or 1,3,6-hexanetriol, followed by amination of the terminal hydroxyl groups.

Examples of such polyoxyalkylene triamines are Jeffamine T-403, Jeffamine T-50000 and Jeffamine XTJ-509; Polyetheramine T 403 and T 5000.

Corresponding diamines may be prepared in similar way starting from diol initiators. Alternatively, terminal hydroxy groups of a polyether may be aminated. Further, terminal amines may be obtained by reductive amination of aldehydes or ketones. Such reactions are well known in the art.

Accordingly, in a preferred aspect, compound B) used as starting material comprising a polyether group is a polyether diamine or polyether triamine based on polyethylene glycol, polypropylene glycol, polyethylene glycol-polypropylene glycol copolymers, polytetramethylene glycol, polytetramethylene glycol-polypropylene glycol copolymers, or polytetramethylene glycol/polypropylene glycol copolymers.

Compound B used as a starting material comprising a segment of an aliphatic polysulfide group may be derived from commercially available Thiokol® polymers. For example, the terminal SH groups may be converted to the amines by addition of allyl amines by conventional methods.

Compounds B) may also be used in a form, wherein the amino groups are protected with a protecting group, as described herein-before.

Compound B) may be a mixture of different compounds B). Preferably, compound B) may be a mixture of a compound B) having a silicon-functional group and a compound B) comprising a segment selected from a polyether group or an organic polysulfide group, preferably a segment of a polyether group.

For example, the weight ratio of compound B) with a silicon-functional group and compound B) comprising a segment selected from a polyether group or an organic polysulfide group may be 5:95 to 50:50.

Preferably, the weight ratio of compound B) with a silicon-functional group and compound B) comprising a segment a polyether group may be 5:95 to 50:50.

A suitable compound C) used as starting material comprising a segment of a polyether group or an organic polysulfide group may be a compound based on a polyether group or an organic polysulfide group having at least 2 terminal non-aromatic, ethylenically unsaturated groups, preferably 2 to 6 non-aromatic, ethylenically unsaturated groups.

Preferred are compounds C) having (meth)acrylate groups or vinyl groups, more preferably (meth)acrylate groups.

Most preferred are compounds C) used as starting material comprising a segment of a polyether group which are polyether-di(meth)acrylates or polyether-tri(meth)acrylates.

Polyether(meth)acrylates are, for example, based on polyethylene glycol, polypropylene glycol, polypropylene glycol/polyethylene glycol copolymers, polytetramethylene glycol, polytetramethylene glycol/polypropylene glycol copolymers, or polytetramethylene glycol/polypropylene glycol copolymers.

A suitable polyether(meth)diacrylate may be defined by formula

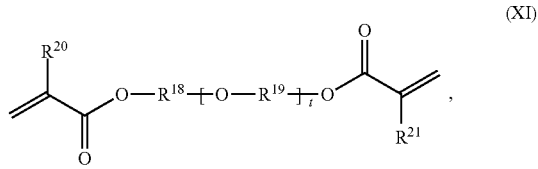

(XI)

$R^{18}$ and $R^{19}$ independently of one another and in each occurrence are $C_2$-$C_4$-alkylene, $R^{20}$ and $R^{21}$ independently of one another are H or methyl, and t may be from 1 to 70, preferably 1 to 40.

Preferably, $R^{18}$ and $R^{19}$ are the same $C_2$-$C_4$-alkylene, for example, ethylene, propylene or butylene.

Preferably, $R^{20}$ and $R^{21}$ are the same, more preferably $R^{20}$ and $R^{21}$ are $CH_3$.

Accordingly, in a preferred aspect, compound C) used as starting material comprising a polyether group is a polyether-di(meth)acrylate of formula

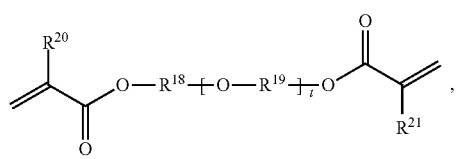

(XI)

$R^{18}$ and $R^{19}$ independently of one another and in each occurrence are $C_2$-$C_4$-alkylene, $R^{20}$ and $R^{21}$ independently of one another are H or methyl, and t may be from 1 to 70, preferably 1 to 40.

The polyether(meth)acrylates may be a polyethertri(meth)acrylates, and may be ethylene oxide, propylene oxide or butylene oxide based, or mixtures thereof, and may be prepared by reaction thereof with a triol initiator, e.g., glycerol, trimethylolpropane, trimethylolethane or 1,3,6-hexanetriol, followed by reaction of the terminal hydroxyl groups with (meth)acrylic acid or derivatives thereof. The reaction is well known in the art.

Corresponding di(meth)acrylates may be prepared in similar way starting from diol initiators. Alternatively, terminal hydroxy groups of a polyether may be reacted with (meth)acrylic acid or derivatives thereof. Such reactions are well known in the art.

Accordingly, in a preferred aspect, compound C) used as starting material comprising a polyether group is a polyether-di(meth)acrylate or polyether-tri(meth)acrylate based on polyethylene glycol, polypropylene glycol, poly-ethylene glycol-polypropylene glycol copolymers, polytetramethylene glycol, polytetramethylene glycol-polypropylene glycol copolymers, or polytetramethylene glycol/polypropylene glycol copolymers.

Compound C) used as a starting material comprising a segment of an aliphatic polysulfide group, for example, of formula (IX), may be derived from commercially available Thiokol® polymers. The terminal SH groups may be reacted with acetylenes to obtain terminal vinyl group. Epoxy-terminated polysulfides, which are, for example, commercially available, may be converted with (meth)acrylic acids or derivatives thereof.

Compound C) may be a mixture of different compounds C). Preferably, compound C) may be a mixture of a compound C) having a silicon-functional group and a compound C) comprising a segment selected from a polyether group or an organic polysulfide group, preferably a segment of a polyether group.

For example, the weight ratio of compound C) with a silicon-functional group and compound C) comprising a segment selected from a polyether group or an organic polysulfide group may be 5:95 to 50:50.

Preferably, the weight ratio of compound C) with a silicon-functional group and compound C), which is a polyether-di(meth)acrylate or polyether-tri(meth)acrylate may be 5:95 to 50:50.

According to the process of this invention a compound A) with at least one five-membered cyclic monothiocarbonate group and a compound B) with at least one amino group, selected from primary or secondary amino groups or blocked primary or secondary amino groups, hereinafter referred to as amino groups, and optionally a compound C) with at least one functional group, that reacts with a group —SH, are used as starting materials, wherein at least one of the compounds used as starting material comprises a silicon-functional group.

The principles of the reaction of compounds A), B) and optionally C) as well as details of the parameters of the reaction are described in WO 2019/034470 A1 and WO 2019/034473 A1.

The ring system of the five-membered cyclic monothiocarbonate group of compound A) is opened by the amino group of compound B), resulting in an adduct comprising a urethane group and a group —SH.

The group —SH of the adduct may be further reacted with a —SH reactive group, notably a non-aromatic ethylenically unsaturated group or an epoxy group of compound C) or also of compounds A) and B) as there exist also compounds A) or B) that comprise a non-aromatic, ethylenically unsaturated group, for example, 5-(methacryloyloxy)methyl-1,3-oxathiolane-2-one or 5-(acryloyloxy)methyl-1,3-oxathiolane-2-one (compounds C), allyl amine or aminoalkylvinylether (compounds B).

The group —SH reacts with the —SH reactive group. For example, the addition of a non-aromatic, ethylenically unsaturated group to —SH is known as Michael addition or thiol-ene reaction.

It should be mentioned that groups —SH that are not reacted may oxidize and will form disulfide bridges. Such oxidation may occur at room temperature in the presence of oxygen or other oxidants. Disulfide bridges may improve mechanical properties of the polymers obtained.

Compounds B) are preferably used in an amount to have 0.8 to 1.2 mol of amino groups of compound B) per 1 mol of five-membered cyclic monothiocarbonate groups of compound A) in the reaction mixture.

Preferably, the amount of functional groups that react with —SH is 0.5 to 1.2 mol per 1 mol of five-membered cyclic monothiocarbonate groups of compound A).

Preferably, the functional groups that react with —SH are groups of compound C).

Preferably, the starting materials are compounds A), B) and C).

Examples for combinations of compounds A), B) and C) that are reacted in the process steps are listed below, wherein the functional groups are abbreviated as follows:

Cyclic monothiocarbonate group of compound A): CTC
Primary amino group of compound B): PA
Functional group that reacts with —SH of compound C), A) or B): FG
Silicon-functional group: SIL a compound A) with one CTC, a compound B) with one PA and one SIL and a compound C) with one to six FG, preferably 2 to 3 FG;

a compound A) with one CTC, a compound B) with at least two PA and a compound C) with one FG and one SIL;

a compound A) with one CTC, a compound B) with at least two PA and a compound B) with one PA and one SIL;

a compound A) with one CTC, a compound B) with at least two PA, a compound C) with one FG and one SIL and a compound C) with two FG.

Preferably, compounds A), B) and optionally C) are selected to give a mixture of A), B) and optionally C) that is liquid at 21° C., 1 bar. Such mixture does not require additional solvents to become liquid. For a liquid mixture of A), B) and optionally C) it is sufficient that at least one, preferably two of the compounds A), B) and C) are liquid and thus are solvents for the remaining solid compound A), B) or C).

The mixture of compounds A), B) or optionally C) may comprise solvents. In a preferred embodiment no solvent is required.

Compounds A), B) and optionally C) are processed by process step b) to obtain the prepolymer.

In process step b) compounds A) and B) and optionally C) are reacted to form a prepolymer. Process step b) is performed under exclusion of water. To avoid any humidity process step b) may be performed under inert gas. The obtained prepolymer comprises silicon-functional groups that are still curable by water, notably humidity.

The reaction of step b) between compounds A), B) and optionally C) starts usually already at room temperature (about 20-25° C.) and may be completed at room temperature. The reaction may be supported by increasing the temperature of the composition, for example, up to 100° C. Alternatively or in addition, any activation energy for the reactions may be provided by high-energy radiation such as visible or UV-light. It is an advantage of the invention that the reaction easily occurs at low temperature and does not require supply of significant further energy such as high temperatures or high energy radiation.

In case of compounds C) having vinyl or ethinyl groups, a radical initiator should be added.

Accordingly, in a further aspect the invention relates to a prepolymer obtainable by the process steps a) and b), as defined herein in any aspect.

Thus, the invention relates to a prepolymer comprising a urethane group and a curable silicon-functional group, obtainable by a process, which process comprises a) a compound A) with at least one five-membered cyclic monothiocarbonate group and a compound B) with at least one amino group, selected from primary or secondary amino groups or blocked primary or secondary amino groups, and optionally a compound C) with at least one functional group that reacts with a group —SH, are used as starting materials, wherein at least one of the compounds used as starting material comprises a silicon-functional group, and wherein compounds A), B) and optionally C) are processed by b) reacting compounds A) and B) and optionally C) under exclusion of water to obtain a prepolymer with silicon-functional groups that are curable.

The instant process may also provide a composition comprising one or more prepolymers comprising a urethane group and a curable silicon-functional group.

Accordingly, in a further aspect the invention relates to a composition comprising one or more prepolymers comprising a urethane group and a curable silicon-functional group, obtainable by the process steps a) and b), as defined herein in any aspect.

Thus, the invention relates to a composition comprising one or more prepolymers comprising a urethane group and a curable silicon-functional group, obtainable by the process, which process comprises a) a compound A) with at least one five-membered cyclic monothiocarbonate group and a compound B) with at least one amino group, selected from primary or secondary amino groups or blocked primary or secondary amino groups, and optionally a compound C) with at least one functional group that reacts with a group —SH, are used as starting materials, wherein at least one of the compounds used as starting material comprises a silicon-functional group, and wherein compounds A), B) and optionally C) are processed by b) reacting compounds A) and B) and optionally C) under exclusion of water to obtain a prepolymer with silicon-functional groups that are curable.

The obtained prepolymer comprises as structural element a urethane group with a sulfur atom being bonded via an ethylene group to the oxygen of the urethane group. This structural element may be represented by the following general formula:

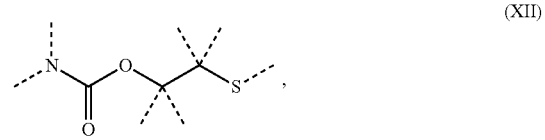

(XII)

wherein all dashed bonds may carry any possible substituents.

The structural element corresponds to a reaction product of a compound A) and a compound B).

Accordingly, in a further aspect the invention relates to a prepolymer comprising (a) a divalent group of formula

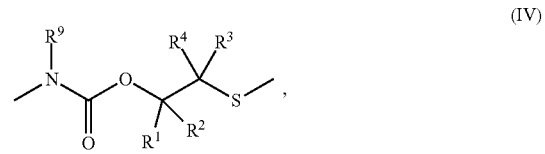

(IV)

wherein $R^1$ is $R^{1a}$ or $R^{1b}$, $R^2$ is $R^{2a}$ or $R^{2b}$, $R^3$ is $R^{3a}$ or $R^{3b}$, $R^4$ is $R^{4a}$ or $R^{4b}$, $R^{1a}$ to $R^{4a}$ are independently from one another are hydrogen or an organic group with up to 50 carbon atoms, or, alternatively, $R^{2a}$, $R^{4a}$ and the two linking carbon atoms together form a five to ten membered carbon ring;

$R^{1b}$ to $R^{4b}$ independently from one another are hydrogen or an organic group with up to 50 carbon atoms, wherein, alternatively, $R^{2b}$, $R^{4b}$ and the two carbon atoms of the monothiocarbonate group may also together form a five to ten membered carbon ring, and one of the groups $R^{1b}$ to $R^{4b}$ is a linking group to Z, n is an integral number of at least 2, Z is a n-valent organic group;

$R^9$ is hydrogen or $C_1$-$C_4$-alkyl or $C_1$-$C_4$-alkylene-N($C_1$-$C_4$alkyl)$_2$, and (b) a curable silicon-functional group.

Preferably, the prepolymer is derived from compound A) of formula (I). Thus, the prepolymer comprises (a) a group of formula

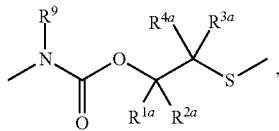

(IVa)

wherein $R^{1a}$ to $R^{4a}$ are independently from one another are hydrogen or an organic group with up to 50 carbon atoms, or, alternatively, $R^{2a}$, $R^{4a}$ and the two linking carbon atoms together form a five to ten membered carbon ring;

$R^9$ is hydrogen or $C_1$-$C_4$-alkyl or $C_1$-$C_4$-alkylene-N($C_1$-$C_4$alkyl)$_2$, and (b) a curable silicon-functional group.

Preferably, the organic group of $R^{1a}$ to $R^{4a}$ is an alkyl group, a group —$CH_2O$—$R^{5a}$ or a group —$CH_2O$—C(=O)—$R^{6a}$, wherein $R^{5a}$ and $R^{6a}$ are an alkyl group with 1 to 10 carbon atoms.

More preferably, two to all four of $R^{1a}$ to $R^{4a}$ in formula (IVa) are hydrogen, and the remaining groups $R^{1a}$ to $R^{4a}$ are an organic group, preferably selected from an alkyl group, a group —$CH_2$—O—$R^{5a}$ or a group —$CH_2O$—C(=O)—$R^{6a}$.

Most preferably, three of $R^{1a}$ to $R^{4a}$ in formula (IVa) are H, and the remaining groups $R^{1a}$ to $R^{4a}$ are an organic group, especially an alkyl group, a group —$CH_2O$—$R^{5a}$ or a group —$CH_2O$—C(=O)—$R^{6a}$. In particular, $R^{1a}$ or $R^{2a}$ is the remaining group representing an organic group, especially an alkyl group, a group —$CH_2$—O—$R^{5a}$ or a group —$CH_2O$—C(=O)—$R^{6a}$.

The group $R^9$ is preferably hydrogen or $C_1$-$C_4$-alkyl, more preferably hydrogen.

In a preferred aspect, the prepolymer comprises a curable silicon-functional group of formula

 (III), wherein at least one of the groups $R^{1s}$ to $R^{3s}$ is an alkoxy group and the other groups $R^{1s}$ to $R^{3s}$ are hydrogen, an alkyl group or an alkylene-vinyl group.

More preferably, two or three of the groups $R^{1s}$ to $R^{3s}$ are a $C_1$-$C_4$-alkoxy group, and the remaining groups $R^{1s}$ to $R^{3s}$ are a $C_1$-$C_4$-alkyl group or a $C_1$-$C_2$alkylene-vinyl group, especially one alkyl group.

More preferably, two or three of the groups $R^{1s}$ to $R^{3s}$ are an alkoxy group and any remaining group $R^{1s}$ to $R^{3s}$ is an alkyl group or alkylene-vinyl group. For example, two or three of the groups $R^{1s}$ to $R^{3s}$ are methoxy or ethoxy, and any remaining group $R^{1s}$ to $R^{3s}$ is methyl, ethyl, vinyl or allyl.

Most preferably, two of the groups $R^{1s}$ to $R^{3s}$ are a $C_1$-$C_4$-alkoxy group and any remaining group $R^{1s}$ to $R^{3s}$ is a $C_1$-$C_4$-alkyl group.

One of the starting materials may comprise a segment selected from a polyether group or an organic polysulfide group.

Accordingly, in a preferred aspect, the prepolymer comprises the segment (c) selected from a polyether group or an organic polysulfide group.

The prepolymer preferably comprises a segment (c) selected from a polyether group or an organic polysulfide group in an amount of from 40 to 95 wt %, based on the total weight of the prepolymer, more preferably of from 50 to 90 wt %, most preferably 55 to 90 wt %.

Thus, a prepolymer comprising a urethane group and a curable silicon-functional group is preferred, wherein the prepolymer comprises a segment (C) of a polyether group having units of formula

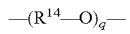 (VIII), wherein $R^{14}$ is a divalent, straight or branched alkylene group containing 1 to 14 carbon atoms, preferably a straight or branched alkylene group of 2 to 4 carbon atoms, for example, ethylene, propylene or butylene, and q is 2 to 70, preferably 2 to 40; or a segment (C) of an organic polysulfide group comprising an aliphatic polymer group derived from an aliphatic polysulfide polymer, obtainable by reaction of 2-chloroethanol, formaldehyde and $Na_2S_2$ or by reaction of bischloroethylformal and $Na_2S_2$.

More preferred is a prepolymer comprising a urethane group and a curable silicon-functional group, wherein the prepolymer comprises a segment (C) of a polyether group having units of formula

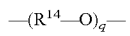 (VIII), wherein $R^{14}$ is a divalent, straight or branched alkylene group containing 1 to 14 carbon atoms, preferably a straight or branched alkylene group of 2 to 4 carbon atoms, for example, ethylene, propylene or butylene, and q is 2 to 70, preferably 2 to 40.

Most preferred is a prepolymer comprising a urethane group and a curable silicon-functional group, wherein the prepolymer comprises a segment (C) of a polyether group having units of formula (VIII), which are derived from compound B) and/or C) used as starting materials, especially compound B) or C), in particular compound B).

Desirably, the prepolymer comprises a segment (c) of a polyether group in an amount of from 50 to 95 wt %, based on the total weight of the prepolymer, more preferably of from 55 to 90 wt %.

The prepolymer usually comprises a silicon content of 0.001 to 0.3 mol per 100 g of prepolymer.

Preferably, the content of silicon in the prepolymer is 0.001 to 0.4 mol Si per 100 g of the prepolymer, more preferably 0.005 to 0.2 mol Si, most preferably 0.01 to 0.15 mol Si.

The content of Si applies to the prepolymer obtained in step b) as well as to the cross-linked polymer finally obtained by process steps b) and b2).

The silicon content (in mol) is calculated based on the used amounts of the starting materials, i.e., as silicon/total weight of the starting materials.

The prepolymer may be derived from compound A) and compound B) or from compound A), compound B) and compound C).

The prepolymer which is derived from compound A) and compound B) contains usually a disulfide group, a curable silicon-functional group and optionally a segment selected from a polyether group or an organic polysulfide group.

For example, the prepolymer may be derived from a compound A) of formula (I), a monoamine containing a curable silicon-functional group and a polyetherdiamine. The prepolymer may comprise the following elements of formulae

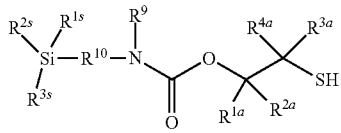
(XII)

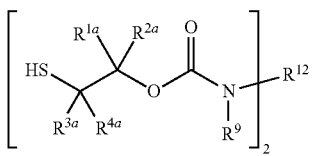
(XIII)

which may be linked by disulfide groups via the SH groups, wherein
$R^{1a}$ to $R^{4a}$ are independently from one another are hydrogen or an organic group with up to 50 carbon atoms,
two or three of the groups $R^{1s}$ to $R^{3s}$ are a $C_1$-$C_4$-alkoxy group, and the remaining groups $R^{1s}$ to $R^{3s}$ are a $C_1$-$C_4$-alkyl group or a $C_1$-$C_2$-alkylene-vinyl group, especially one alkyl group;
$R^9$ is hydrogen, $C_1$-$C_4$-alkyl or $C_1$-$C_4$-alkylene-N($C_1$-$C_4$alkyl)$_2$,
$R^{10}$ is a $C_1$-$C_{18}$-alkylene group, which is optionally interrupted by O, S, or $NR^{13}$, and
$R^{12}$ is a bivalent polyether group or organic polysulfide group.

The prepolymer may preferably comprise the elements of formulae (XII) and (XIII),
wherein
two of the groups $R^{1s}$ to $R^{3s}$ are a $C_1$-$C_4$-alkoxy group and any remaining group $R^{1s}$ to $R^{3s}$ is a $C_1$-$C_4$-alkyl group;
$R^{1a}$ is an organic group selected from an alkyl group, a group —CH$_2$—O—$R^{5a}$ or a group —CH$_2$O—C(=O)—$R^{6a}$;
$R^{2a}$ to $R^{4a}$ are H;
$R^{5a}$ and $R^{6a}$ are an alkyl group with 1 to 10 carbon atoms;
$R^9$ is H or methyl or ethyl;
$R^{10}$ is $C_2$-$C_8$-alkylene, more preferably $C_3$-$C_6$-alkylene; and
$R^{12}$ is a bivalent polyether group.

For example, the weight ratio of compound B) with the silicon-functional group and compound B) comprising a segment of the polyether group may be 5:95 to 50:50.

The prepolymer may be derived from compound A), compound B) and compound C).

Accordingly, in a preferred aspect the invention relates to a prepolymer, which prepolymer comprises a group of formula

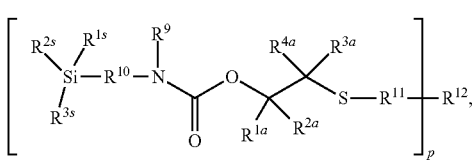
(V)

wherein
$R^9$ is hydrogen, $C_1$-$C_4$-alkyl or $C_1$-$C_4$-alkylene-N($C_1$-$C_4$alkyl)$_2$,
$R^{10}$ is a $C_1$-$C_{18}$-alkylene group, which is optionally interrupted by O, S or $NR^{13}$, $R^{11}$ is a group derived from a non-aromatic, ethylenically unsaturated group,
$R^{12}$ is a p-valent polyether or an organic polysulfide group;
$R^{13}$ is hydrogen or $C_1$-$C_4$-alkyl;
p is an integral number of 2 to 6, preferably 2 or 3;
or a group of formula

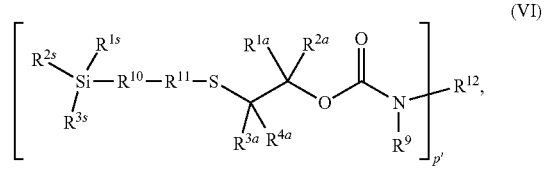
(VI)

wherein
$R^9$ is hydrogen or $C_1$-$C_4$-alkyl,
$R^{10}$ is a $C_1$-$C_{18}$-alkylene group, which is optionally interrupted by O, S or $NR^{13}$,
$R^{11}$ is a group derived from a non-aromatic, ethylenically unsaturated group,
$R^{12}$ is a p'-valent polyether group or an organic polysulfide group;
$R^{13}$ is hydrogen or $C_1$-$C_4$-alkyl;
p' is an integral number of 2 to 5, preferably 2 to 3.
Alternatively preferred, p and p' are 2.
The group $R^{10}$ is $C_1$-$C_{18}$-alkylene group or a $C_1$-$C_{18}$-alkylene group, which is interrupted one or more times by O, S or $NR^{13}$, preferably 1, 2 or 3 times.
Preferably, $R^{12}$ a bi- or trivalent polyether group having units of formula $$-(R^{14}-O)_q-$$ (VIII), wherein $R^{14}$ is a divalent, straight or branched alkylene group containing 1 to 14 carbon atoms, preferably a straight or branched alkylene group of 2 to 4 carbon atoms, for example, ethylene, propylene or butylene, and
q is 2 to 70, preferably 2 to 40; or
a bi- or trivalent organic polysulfide group comprising an aliphatic polymer group derived from an aliphatic polysulfide polymer, obtainable by reaction of 2-chloroethanol, formaldehyde and Na$_2$S$_2$ or by reaction of bischloroethylformal and Na$_2$S$_2$.
More preferably, $R^{12}$ is a bi- or trivalent polyether group having units of formula $$-(R^{14}-O)_q-$$ (VIII), wherein $R^{14}$ is a divalent, straight or branched alkylene group containing 1 to 14 carbon atoms, preferably a straight or branched alkylene group of 2 to 4 carbon atoms, for example, ethylene, propylene or butylene, and
q is 2 to 70, preferably 2 to 40.
In particular, $R^{11}$ is a group derived from a vinyl group, an ethinyl group or a (meth)acrylic group, especially a vinyl group or a (meth)acrylic group, in particular a methacrylic group.
The group of formula (V) comprises monomer units derived from compound A), compound B) and compound C), wherein
compound A) is of formula (I),
compound B) is formula $R^{1s}R^{2s}R^{3s}Si$—$R^{10}$—$NR^9H$
compound C) is of formula $R^{11}$—$(R^{12})_p$,
$R^9$ is hydrogen, $C_1$-$C_4$-alkyl or $C_1$-$C_4$-alkylene-N($C_1$-$C_4$alkyl)$_2$, $R^{10}$ is a $C_1$-$C_{18}$-alkylene group, which is optionally interrupted by O, S or $NR^{13}$,
$R^{11'}$ is a non-aromatic, ethylenically unsaturated group,
$R^{11}$ is a group derived from a non-aromatic, ethylenically unsaturated group,
$R^{12}$ is a p-valent polyether group or p-valent organic polysulfide group;
$R^{13}$ is hydrogen or $C_1$-$C_4$-alkyl; and
p is an integral number of 2 to 6, preferably 2 or 3;

The group of formula (VI) comprises monomer units derived from compound A), compound B) and compound C), wherein
compound A) is of formula (I),
compound B) is of formula $(R^{12})_{p'}$—$NR^9H$,
compound C) is of formula $R^{1s}R^{2s}R^{3s}Si$—$R^{10}$—$R^{11'}$,
$R^9$ is hydrogen, $C_1$-$C_4$-alkyl or $C_1$-$C_4$-alkylene-$N(C_1$-$C_4$alkyl$)_2$,
$R^{10}$ is a $C_1$-$C_{18}$-alkylene group, which is optionally interrupted by O, S or $NR^{13}$,
$R^{11'}$ is a non-aromatic, ethylenically unsaturated group,
$R^{11}$ is a group derived from a non-aromatic, ethylenically unsaturated group,
$R^{12}$ is a p'-valent polyether group or a p'-valent organic polysulfide;
$R^{13}$ is hydrogen or $C_1$-$C_4$-alkyl; and
p' is an integral number of 2 to 5, preferably 2 to 3.

More preferred is a prepolymer of formula (V), wherein
$R^9$ is hydrogen or $C_1$-$C_4$-alkyl, preferably hydrogen or methyl, especially hydrogen,
$R^{10}$ is a $C_2$-$C_8$-alkylene group, more preferably a $C_2$-$C_6$-alkylene group,
$R^{11}$ is a group derived from a non-aromatic, ethylenically unsaturated group,
$R^{12}$ is a p-valent polyether group;
p is an integral number of 2 to 3;
or a prepolymer of formula (VI), wherein
$R^9$ is hydrogen or $C_1$-$C_4$-alkyl, preferably hydrogen or methyl, especially hydrogen,
$R^{10}$ is a $C_2$-$C_8$-alkylene group,
$R^{11}$ is a group derived from a non-aromatic, ethylenically unsaturated group, and
$R^{12}$ is a p'-valent polyether group;
p' is an integral number of 2 to 3.
Alternatively preferred, p and p' are 2.

In particular, $R^{11}$ is a group derived from a vinyl group, an ethinyl group or a (meth)acrylic group, especially a vinyl group or a (meth)acrylic group, in particular a methacrylic group.

The prepolymer comprising curable silicon-functional groups may be further reacted. The prepolymer obtained in step b) is brought into the desired form, which is a coating, a filling or any other three-dimensional body. The silicon-functional groups cross-link with each other in the presence of any ambient water, for example, humidity or water supplied. Usually the normal humidity is sufficient to final get a fully cross-linked polymer. The cross-linking process may be accelerated by providing further water. For example, water may be added to the prepolymer shortly before starting step b2).

Accordingly, in a further aspect, the invention relates to a process for preparing a cross-linked polymer comprising urethane groups and siloxane linkages, which process comprises
step a) and b), as defined herein in any aspect; and
step b2) applying the prepolymer obtained in step b) to a surface, gap or a three-dimensional template and curing the silicon-functional group with ambient water.

The polymer obtained in step b2) is a fully cured polymer having siloxane linkages.

Accordingly, in a further aspect, the invention relates to a cross-linked polymer comprising monomer units derived from compound A), compound B) and optionally compound C), as defined in any aspect herein,
wherein the polymer comprises 0.001 to 0.3 mol of silicon per 100 g of the cross-linked polymer.

Preferably, the content of silicon in the cross-linked polymer is 0.001 to 0.4 mol Si per 100 g of the cross-linked polymer, more preferably 0.005 to 0.2 mol Si, most preferably 0.01 to 0.15 mol Si.

In a further aspect, the invention relates to a cross-linked polymer obtainable by the process, which process comprises
step a) and b), as defined herein in any aspect; and
step b2) applying the prepolymer obtained in step b) to a surface, gap or a three-dimensional template and curing the silicon-functional group with ambient water.

The instant prepolymer may be used in compositions for various applications, for example, in a one-component sealant or adhesive composition. Preferably, the prepolymer is used in a one-component sealant or adhesive composition.

Accordingly, the invention relates to a composition comprising a prepolymer, as defined in any aspect herein.

In a preferred aspect, the invention relates to a one-component sealant or adhesive composition comprising a prepolymer, as defined in any aspect herein.

Usually, the composition, preferably the one-component sealant or adhesive composition, comprises the prepolymer in a sufficient amount such that the sealant or adhesive is capable of sealing onto a substrate or bonding two substrates together, for example, in an amount of from 10 to 100 wt %, based on the total weight of the composition, preferably 20 to 70 wt %.

The one-component sealant or adhesive composition usually contains additives which are well known in the art. Further solvents may be present to reduce the viscosity.

If present, the solvents should be non-aqueous and non-reactive with the prepolymer at the intended level of use. Examples include tetrahydrofuran, dimethylformamide, dimethylacetamide, N-methylpyrrolidone, methyl ethyl ketone, acetone, heptane, toluene, trichloroethane, methyl acetate, butyl acetate, t-butyl acetate and the like. Mixtures of said solvents may also be used. Solvents may be present in an amount of from 0 to 30 wt %, preferably 0 to 15 wt %, based on the total weight of the composition.

Examples of suitable additives are catalysts, radical initiators, dehydrating agents, plasticizers, fillers, thixotropic modifiers, adhesion promoters, stabilizers or additives that are desired or necessary for the intended final use of the cross-linked polymer, for example, colorants or dielectric substances.

Examples of suitable catalysts, preferably silanol condensation catalysts, are, for example, organotin compounds such as tin(II)-2-ethylhexanoate, dioctyltin dilaureate, dibutyltin dilaureate, dibutyltin maleate or dibutyltin diacetate; fluorine-containing compounds, such as triethoxyfluorosilane; tertiary amines such as 1,8-diazabicyclo(5.4.0)undec-7-ene (DBU), 1-azabicyclo[3.3.0]octane, 1,4-diazabicyclo[2.2.2]octane, trialkylamines or N-substituted piperidines; titanates such as alkyl titanates or organosilicon titanates; or combinations thereof.

Preferably, a silanol condensation catalyst is present, generally in an amount sufficient to cure the polymer upon exposure to humidity, for example, in an amount of from 0.005 to 5 wt %, based on the total weight of the prepolymer to be cured, preferably of from 0.1 to 2 wt %. The catalysts may be added during or after the preparation of the prepolymers.

Alternatively preferred is that no silanol condensation catalyst is present.

Examples of suitable dehydrating agents are, for example, vinyl silanes such as vinyltrimethoxy silane or vinyl triethoxy silane, in an amount of from 0 to 5 wt %, based on the total weight of the composition, preferably 0 to 3 wt % or 0.1 to 2 wt %.

Examples of suitable plasticizers are, for example, phthalates such as dioctyl phthalate, dibutyl phthalate, diundecyl phthalate, or dibutyl benzyl phthalate, adipates such as dialkyl adipates, phosphates such as trioctyl phosphate or tricresyl phosphate, or sulfonamides such as N-butyl-p-toluene-sulfonamide. Plasticizers are preferably used in an amount of from 0 to 30 wt %, based on the total weight of the composition, more preferably 5 to 20 wt %.

Examples of suitable fillers are, for example, reinforcing fillers, such as silica, fumed silica like Aerosol®, silica aerogels, clays, calcium carbonate, titanium dioxide, talc, magnesium carbonate or glass fibers. Examples of colorants are, for example, pigments or dyes, like carbon black, preferably transparent pigments or dyes. Examples of dielectric substances are, for example, graphite or carbon black.

The total amount of fillers, colorants and dielectric substances is generally about 0 to 60 wt %, based on the total weight of the composition, preferably 5 to 50 wt %.

Examples of suitable thixotropic agents are, for example, alumina, limestone, zinc oxide, sulfur oxides, calcium carbonate, perlite, NaCl or cyclodextrin. The total amount of thixotropic agents is generally about 0 to 10 wt %, based on the total weight of the composition, preferably 0 to 2 wt %, more preferably 0.1 to 2 wt %.

Suitable stabilizers are, for example, biozides, UV stabilizers, heat stabilizers or antioxidants. Examples are sterically hindered phenols, thioethers, substituted benzotriazoles, sterically hindered amines of the HALS type or combinations thereof. Stabilizers are usually present in an amount of from 0 to 2.5 wt %, based on the total weight of the composition.

The additives may be added to the prepolymer before, during or after their preparation. The additives should be added in dried form and under substantially anhydrous conditions. The components of the composition may be blended in a suitable mixer under inert atmosphere in the absence of oxygen and atmospheric moisture. Once the one-component sealant or adhesive composition is formulated, it is packaged in a suitable container such that it is protected from atmospheric moisture and oxygen.

A variety of substrates may be sealed or bonded using the instant one-component sealant or adhesive composition. Examples include plastics, glass, wood, ceramics, metal, coated substrates, for example, primer-coated substrates. Forms may be a surface, a gap or a three-dimensional template.

The adhesive composition is applied to a substrate and the adhesive composition on the first substrate is thereafter contacted with a second substrate.

Generally, the one-component sealant or adhesive composition is applied to a substrate at ambient temperature in the presence of atmospheric moisture. Exposure to atmospheric moisture is sufficient to result in curing of the sealant or adhesive composition leading to the instant cross-linked polymer. The cured product becomes tack-free within a relatively short period of time.

The one-component sealant or adhesive composition may also be applied onto wet or moist surfaces.

Curing may be accelerated by adding additional water or by applying heat. Preferably, the sealant or adhesive composition is formulated to provide a working time of up to 3 bis 8 hours dependent on the content of moisture. The complete curing may need up to 5 days.

The cross-linked polymer is suitable for use as a component of a sealant or adhesive.

Accordingly, in a further aspect, the invention relates to the use of the cross-linked polymer, as defined in any aspect herein-before, as a component of a sealant or an adhesive.

For example, the instant compositions are suitably applied in the construction, architectural, transportation such as automotive industry.

With the processes of the invention silyl-modified polymers with urethane and sulfur functionality are obtained easily and economically. All of these groups combine specifically desired properties useful for producing sealant and adhesives.

The prepolymers of the present invention may be easily and economically accessed by the instant process. The process may be performed at room temperature without further supply of energy. The process does not require the use of isocyanates or starting materials with mercaptan groups.

The process offers the possibility to prepare a variety of products, notably polymer hybrids having the benefits resulting from the content of sulfur, urethane and silyl cross-linking, which are, for example, mechanical properties in combination with chemical resistance, barrier properties, anti-static and anti-corrosion properties.

The cross-linked polymers, especially having a soft segment of a polyether group or an organic polysulfide group, have good elasticity properties, show high flexibility and transparency, if only filled with transparent fillers or pigments.

Curing may be done rapidly at room temperature without significant shrinkage to tack-fee products. Further, the cross-linked polymers show a high refractive index, which is of advantage, for example, within glass substrates.

The cross-linkages derived from the inorganic silicon-functional groups present within the prepolymer promote tenacious adhesion of the cross-linked polymer hybrid to various substrates like glass or metals, where usually primers are needed.

Due to the nature of the silyl substituents and the concentration of the silyl groups in the prepolymer the properties may be tailor-made for use to prepare one-component sealant or adhesive compositions. The prepolymers may be obtained after precuring under nitrogen atmosphere as a viscous and storable material.

The prepolymers remain stable under anhydrous storage conditions for a long period of time. Moreover, the alkoxy-hydrolysable groups on the terminal silicon-function are preferable to other hydrolysable groups, since they yield an inert by-product of alcohol upon curing in the presence of moisture.

The one-component sealant or adhesive compositions do not suffer the drawbacks encountered in on-site mixing of viscous materials, which once mixed must be used quickly before they become unmanageable.

The definitions and preferences given for the pigment mentioned herein-before apply in any combination as well as in any combination for the other aspects of the invention.

The present invention will now be explained in more detail with reference to the following examples. These examples should not be construed as limited. Unless otherwise stated, "%" is always % by weight (wt %).

EXAMPLES

Shore A Hardness

Hardness measurements were conducted with a Shore A hardness tester HDA 100-1 (Sauter GmbH). The 3 mm samples were placed on a hard surface, and the hardness was tested on four different locations on the sample surface. The average of the four values is given as the hardness for comparison between different samples.

Viscosity

Viscosities were measured on a MCR 301 rheometer (Anton Paar GmbH) in a plate to plate (25 mm) rotational experiment. The shear rate was increased from 1 to 250 1/s at a constant temperature.

Glass Transition Temperature $T_g$

The glass transition temperature was determined by differential scanning calorimetry (DSC) in a temperature range of −170 to 600° C. at a heating rate of 10 k/min in air atmosphere (Perkin-Elmer Pyris-1).

Thermoaraphimetric Analysis (TGA)

The onset temperature $T_{onset}$ was determined in a temperature range of 50-650° C. at a heating rate of 10 K/min in air atmosphere with STA 449 F5 (Netzsch Gerätebau GmbH);

Components Used in Examples

Compound A

A-1 5-(butoxymethyl)-1,3-oxathiolane-2-one, prepared according to Example 3 of WO 2019/034469 A1.

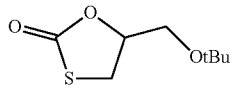 [SMILES: CC(C)(C)OCC1CSC(=O)O1]

A-2 5-methyl-1,3-oxathiolane-2-one, prepared according to Example 1 of WO 2019/034469 A1.

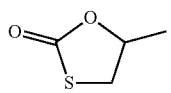

Compound B

B-1 Jeffamine THF-170 amine ($M_n$~1700 g/mol)

An amine based on a [poly(tetramethylene ether glycol)]/(polypropylene glycol) copolymer, available from Huntsman Jeffamine THF-170 (a white solid at room temperature) was melted at 50° C. and cooled again to room temperature before use in the Examples. It remains liquid for several hours.

B2 3-Aminopropyldimethoxymethylsilane

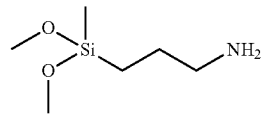

B3 4,9-Dioxa-1,12-dodecanediamine

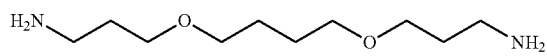

Compound C

C-1 3-(Dimethoxymethylsilyl)propyl methacrylate

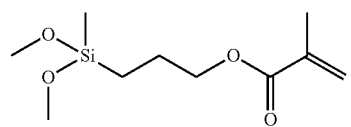

C-2 3-(trimethoxysilyl)propyl methacrylate

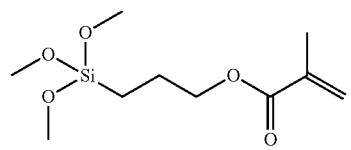 [SMILES: C=C(C)C(=O)OCCC[Si](OC)(OC)OC]

C-3 Poly(propylene glycol) dimethacrylate ($M_n$≈560 g/mol)

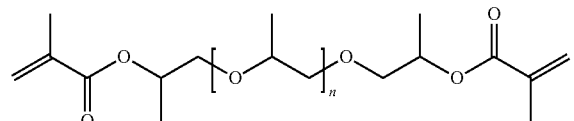

C-4 Diurethane dimethacrylate

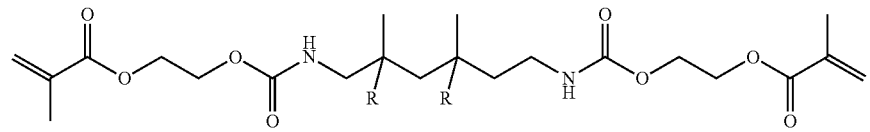

R = H or CH$_3$ (~1:1)

Synthesis Example 1

C-5 Polytetrahydrofuran dimethacrylate (PTHF-DMA, $M_n$~3200 g/mol)

Polytetrahydrofuran ($M_n$~3000 g/mol, 60 g, 20 mmol) was heated in an open flask to 90° C. Then MgO nanoparticles (average particle size: 20 nm, 330 mg, ~0.5 wt %) were added under stirring. After ten min stirring methacrylic anhydride (6.3 mL, 42 mmol, 2.1 eq.) was added in one portion into the open flask. The mixture was cooled to room temperature after 2 hours, diluted with dichloromethane (150 mL) and extracted 3× with aqueous saturated $NaHCO_3$ solution. The separated organic layer was dried over $Na_2SO_4$ until the mixture was clear. The solvent was removed under reduced pressure to yield PTHF-DMA (60 g, approx. 95% yield) as a clear colorless oil which solidifies at room temperature to a white solid. The product was melted at 50° C. and cooled again to room temperature before use in the Examples. It remains liquid for several hours.

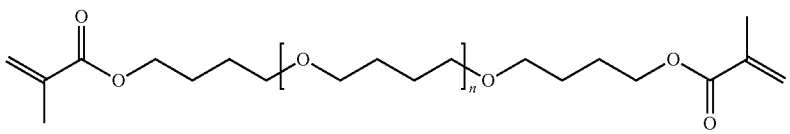

Synthesis Example 2: Synthesis of Compound of Formula (VIIa) in Accordance with the Process Described in WO 2019/034469 A1

First Step: Synthesis of [1-(chloromethyl)-2-(3-trimethoxysilylpropoxy)ethyl]carbonochloridate A 0.25 L stirred tank glass reactor equipped with two condensers (-30° C. and -78° C. (dry ice)) phosgene dip pipe and internal thermometer was purged with dry nitrogen overnight. Afterwards 113.6 g (0.47 mol, 1.00 eq.) of 3-glycidoxypropyltrimethoxysilane were introduced under nitrogen atmosphere. The cooling of the tank reactor was turned on and was adjusted to 15° C. After the reactor reached this temperature, 1.30 g (0.005 mol, 1.00 mol %) of tetrabutylammonium chloride (TBACl) were suspended in the starting material. Afterwards phosgene (overall 61 g, 0.67 mol, 1.31 eq.) was added to the reactor via the dip pipe. The temperature of the reaction mixture was continuously monitored and was kept below 20° C. by carefully adjusting the rate of the phosgene addition. Overall the addition took approximately 4 hours. After the phosgene addition was completed the initial cooling of the reactor was turned off, and the reactor was allowed to slowly reach room temperature. Afterwards the reaction mixture was stirred at room temperature for further 2 hours. Finally, the reaction mixture was stripped, with dry argon at room temperature, phosgene-free within 4 hours. The resulting colorless oil (151 g, 0.45 mol, 96% yield, regioisomeric purity: >95%) was directly used, without further purification, for the thiocarbonate formation.

Second Step: Synthesis of 5-(3-trimethoxysilyl-propoxymethyl)-1,3-oxathiolane-2-one

[1-(chloromethyl)-2-(3-trimethoxysilylpropoxy)ethyl] carbonochloridate (20 g, 0.06 mol) and acetonitrile (50 mL) were placed in a 250 mL 4 neck round bottom flask equipped with a KPG crescent stirrer, dropping funnel, thermometer and a reflux condenser. The solution was cooled down to 0° C. with an ice bath before solid $Na_2S$ (1 eq.) was slowly added, maintaining the temperature at 5° C. After the complete addition the ice bath was removed, and the reaction mixture was allowed to warm to room temperature. After stirring for 4 hours the suspension was filtered, and the solvent was removed under reduced pressure. The crude cyclic thiocarbonate was obtained as a clear oil (17 g, 95%).

Example 1

5-Methyl-1,3-oxathiolane-2-one (295 mg, 2.5 mmol, 1 eq.)
Jeffamine THF-170 (2.13 g, 1.25 mmol, 0.5 eq.)
3-(Dimethoxymethylsilyl)propyl methacrylate (349 mg, 1.50 mmol)
Poly(propylene glycol) dimethacrylate ($M_n$~560 g/mol, 280 mg, 0.5 mmol)

All substances were mixed with a spatula at room temperature (about 20-25° C.) in a glass vial. After homogenization triethoxyfluorosilane (one drop, ~1 mol %) as a silanol condensation catalyst was added under nitrogen-atmosphere, the mixture was mixed again and stored in a glass vail with a lid filled with nitrogen at 80° C. After 24 hours at 80° C. the obtained, viscous prepolymer was transferred into an aluminum mold (60 mm×17 mm×3 mm). The mold was stored at room temperature and ambient air humidity (defined as the curing start time). In intervals of 10 min a tip of a spatula was brought into contact with the surface of the sample. The time until the surface of the sample no longer adhere to the spatula was defined as the time of skin formation. The cured polymer sample was removed from the mold after 48 hours to yield a product which is nearly colorless, fully transparent, very flexible and bendable with close bending radii.

Example 2

5-Methyl-1,3-oxathiolane-2-one (295 mg, 2.5 mmol, 1 eq.)
Jeffamine THF-170 (2.13 g, 1.25 mmol, 0.5 eq.)
3-(Trimethoxysilyl)propyl methacrylate (310 mg, 1.25 mmol)
Poly(propylene glycol) dimethacrylate ($M_n$~560 g/mol, 350 mg, 0.5 mmol)

All substances were mixed with a spatula at room temperature in a glass vial. After homogenization the mixture was stored in the glass vial with a lid filled with nitrogen at 80° C. After 24 hours at 80° C. the obtained, viscous prepolymer was transferred into an aluminum mold (60 mm×17 mm×3 mm). The mold was stored at room temperature and ambient air humidity (defined as the curing start time). In intervals of 10 min a tip of a spatula was brought into contact with the surface of the sample. The time until the surface of the sample no longer adhere to the spatula was defined as the time of skin formation. The cured polymer sample was removed from the mold after 48 hours to yield a product which is nearly colorless, fully transparent, very flexible and bendable with close bending radii.

Example 3

5-Methyl-1,3-oxathiolane-2-one (590 mg, 5.0 mmol)
Diurethane dimethacrylate (1.18 g, 2.5 mmol)
3-Aminopropyldimethoxymethylsilane (816 mg, 5.0 mmol)

All substances were mixed with a spatula at room temperature in a glass vial. After homogenization triethoxyfluorosilane (one drop, ~1 mol %) was added under nitrogen-atmosphere, the mixture was mixed again and stored in a glass vail with a lid filled with nitrogen at 80° C. After 24 hours at 80° C. the obtained, viscous prepolymer was transferred into an aluminum mold (60 mm×17 mm×3 mm). The mold was stored at room temperature and ambient air humidity. The cured polymer sample was removed from the mold after 96 hours to yield a product which is colorless, fully transparent, very flexible and bendable with close bending radii.

Example 4

5-Methyl-1,3-oxathiolan-2-one (590 mg, 5.0 mmol)
Diurethane-dimethacrylate (1.18 g, 2.5 mmol)
3-Aminopropyldimethoxymethylsilane (653 mg, 4.0 mmol)
4,9-Dioxa-1,12-dodecanediamine (102 mg, 0.5 mmol)

All substances were mixed with a spatula at room temperature in a glass vial. After homogenization triethoxyfluorosilane (one drop, ~1 mol %) was added under nitrogen-atmosphere, the mixture was mixed again and stored in a glass vail with a lid filled with nitrogen at 80° C. After 24 hours at 80° C. the obtained, viscous prepolymer was transferred into an aluminum mold (60 mm×17 mm×3 mm). The mold was stored at room temperature and ambient air humidity. The cured polymer sample was removed from the mold after 96 hours to yield a product which is colorless, fully transparent, very flexible and bendable with close bending radii.

Example 5a 5-(Butoxymethyl)-1,3-oxathiolane-2-one (228 mg, 1.2 mmol)
Polytetrahydrofuran dimethacrylate (PTHF-DMA, 1.86 g, 0.6 mmol)
3-Aminopropyldimethoxymethylsilane (157 mg, 0.96 mmol)
Jeffamine THF-170 (204 mg, 0.12 mmol)

All substances were mixed with a spatula at room temperature in a glass vial. After homogenization triethoxyfluorosilane (one drop, ~1 mol %) was added under nitrogen-atmosphere, the mixture was mixed again and stored in a glass vail with a lid filled with nitrogen at 80° C. After 24 hours at 80° C. the obtained, viscous prepolymer was transferred into an aluminum mold (60 mm×17 mm×3 mm). The mold was stored at room temperature and ambient air humidity. The cured polymer sample was removed from the mold after 48 hours to yield a product which is colorless, fully transparent, very flexible and bendable with close bending radii.

Example 5b

The procedure of Example 5a was repeated with the exception of using 3-aminopropyldimethoxymethylsilane in an amount of 118 mg (0.72 mmol) and Jeffamine THF-170 in an amount of 480 mg (0.24 mmol).

Example 6a 5-(Butoxymethyl)-1,3-oxathiolane-2-one (951 mg, 5 mmol)
Poly(propylene glycol) dimethacrylate (1.40 g, 2.5 mmol)
3-Aminopropyldimethoxymethylsilane (653 mg, 4 mmol)
Jeffamine THF-170 (850 mg, 0.5 mmol)

All substances were mixed with a spatula at room temperature in a glass vial. After homogenization triethoxyfluorosilane (one drop, ~1 mol %) was added under nitrogen-atmosphere, the mixture was mixed again and stored in a glass vail with a lid filled with nitrogen at 80° C. After 24 hours at 80° C. the obtained, viscous prepolymer was transferred into an aluminum mold (60 mm×17 mm×3 mm). The mold was stored at room temperature and ambient air humidity. The cured polymer sample was removed from the mold after 48 hours to yield a product which is colorless, fully transparent, very flexible and bendable with close bending radii.

Example 6b

The procedure of Example 6a was repeated with the exception of using 3-aminopropyldimethoxymethylsilane in an amount of 490 mg (3 mmol) and Jeffamine THF-170 in an amount of 1.70 mg (1 mmol).

Example 6c

The procedure of Example 6a was repeated with the exception of using 3-aminopropyldimethoxymethylsilane in an amount of 408 mg (2.5 mmol) and Jeffamine THF-170 in an amount of 2.13 mg (1.25 mmol).

Example 7

5-Methyl-1,3-oxathiolane-2-one (1.48 g, 12.5 mmol)
Jeffamine THF-170 (10.65 g, 6.25 mmol)
3-(Trimethoxysilyl)propyl methacrylate (930 mg, 3.75 mmol)
Poly(propylene glycol) dimethacrylate (2.45 g, 4.38 mmol)
Vinyltrimethoxysilane (310 mg, 2.0 wt % of the polymer)
Tin(II)-2-ethylhexanoate (80 mg, 0.5 wt % of the polymer)
Aerosil® R 972 (2.33 g, 15 wt % of the polymer)

All liquids (Jeffamine THF-170 was preheated to 45° C.) were mixed with a spatula at room temperature in a cup suitable for a speed mixer. After homogenization Aerosil R 972 (filler) was added to the mixture. The closed cup was placed in a speed mixer with 2800 rpm for 1 m. Afterwards the cup was filled with nitrogen and was stored at 65° C. After 24 hours at 65° C. the viscous prepolymer was transferred into an aluminium-mold (60 mm×17 mm×3 mm). The mold was stored at room temperature and ambient air humidity. The cured polymer sample was removed after 48 hours from the mold. The obtained material is colorless, fully transparent, very flexible and bendable with close bending radii.

The polymers obtained in Examples 1 to 4, 5a, 5b, 6a to 6c, 7 and 8 were analysed, and the results are given in Tables 1 and 2.

TABLE 1

|  | Ex.1 | Ex. 2 | Ex. 3 | Ex. 4 | Ex. 5a | Ex. 5b |
|---|---|---|---|---|---|---|
| Time of skin formation [hours] | ~2 | ~2 | ~20 | ~20 | ~16 | ~16 |
| Shore A hardness |  |  |  |  |  |  |
| after 2 days [HA] | 36 | 40 |  |  |  |  |
| after 4 days [HA] |  |  | 72 | 52 | 30 | 20 |
| after 7 days [HA] | 39 | 45 |  |  |  |  |
| Glass transition temp. $T_g$ [° C.] | −68.6 | −69.2 | +15.2 |  | −72.5 | −73.8 |
| TGA (50-650° C.) $T_{onset}$ [° C.] | 363 | 359 | 307 | 309 |  | 373 |
| Si content (wt %/100 g Polymer) | 1.38 | 1.13 | 5.43 | 4.45 | 1.1 | 0.76 |

TABLE 2

|  | Ex. 6a | Ex. 6b | Ex. 6c | Ex. 7 |
|---|---|---|---|---|
| Time of skin formation [hours] | ~16 | ~16 | ~16 | ~2 |
| Shore A hardness |  |  |  |  |
| after 2 days [HA] |  |  |  |  |
| after 4 days [HA] | 55 | 42 | 28 | 43 |
| after 7 days [HA] |  |  |  |  |
| Glass transition temp. $T_g$ [° C.] | −53.1 | −60.7 | −64.9 | −68.1 |
| TGA (50-650° C.) $T_{onset}$ | 337 | 336 |  |  |
| Si content (wt %/100 g polymer) | 2.91 | 1.87 | 1.43 | 0.68 |

The prepolymers obtained in Examples 1 to 4 and 6a to 6c were analysed, and the results of the viscosity analysis are listed in Tables 3 and 4.

TABLE 3

|  | Ex. 1 | Ex. 2 | Ex. 3 | Ex. 4 |
|---|---|---|---|---|
| Viscosity after 24 hours |  |  |  |  |
| at 80° C. [Pa · s] | 5.7 | 2.0 | 0.640 | 0.733 |
| at 65° C. [Pa · s] |  |  |  |  |
| at 50° C. [Pa · s] | 21.7 | 7.1 | 4.9 | 7.3 |
| at 25° C. [Pa · s] | ~97 * | 31.1 | ~55 * | ~140 * |

* The material is strongly shear thinning at 25° C.

TABLE 4

|  | Ex. 6a | Ex. 6b | Ex. 6c |
|---|---|---|---|
| Viscosity after 24 hours |  |  |  |
| at 80° C. [Pa · s] | 0.249 | 0.929 | 1.54 |
| at 65° C. [Pa · s] |  |  |  |
| at 50° C. [Pa · s] | 0.930 | 3.46 | 5.9 |
| at 25° C. [Pa · s] | 4.5 | 16.6 | 28.5 |

Example 8: Preparation of Glued Glass Plates

Example 7 was repeated to obtain the prepolymer. The viscous prepolymer was applied from a syringe onto a glass plate (7.5 cm×2.5 cm×1 mm). A second glass plate was placed on the prepolymer, and the two glass plates were pressed together. The polymer layer was 6.6 µm.

The transmission of the glued glass plates was measured between 200 and 1000 nm. Compared to the transmission of two identical glass plates without adhesive the glass plates glued with the polymer of Example 8 shows an approximately similar transmission and full transparency for visible light, within the error of measurement (see FIGURE).

The invention claimed is:

1. A process for preparing a prepolymer comprising a urethane group and a curable silicon-functional group, the process comprising:
    reacting a compound A) with a compound B), and optionally a compound C), under exclusion of water, to obtain the prepolymer comprising the urethane group and the curable silicon-functional group,
    wherein the compound A) comprises at least one five-membered cyclic monothiocarbonate group, and
    wherein the compound B) comprises at least one amino group, selected from the group consisting of primary amino groups, secondary amino groups, blocked primary amino groups, and blocked secondary amino groups, and
    wherein the compound C), if present, comprises at least one functional group that reacts with a group —SH,
    wherein at least one of the compounds A), B), and optionally C) comprises a silicon-functional group.

2. The process according to claim 1, wherein the compound A) is
    a compound of formula (I),

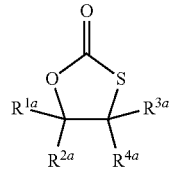

wherein $R^{1a}$ to $R^{4a}$ independently from one another are hydrogen or an organic group with up to 50 carbon atoms, and
    wherein, alternatively, $R^{2a}$, $R^{4a}$, and the two carbon atoms of the thiocarbonate group together form a five to ten membered carbon ring; or
    a compound of formula (II),

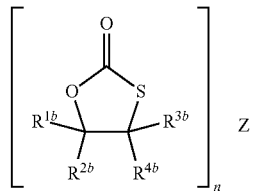

wherein $R^{1b}$ to $R^{4b}$ independently from one another are hydrogen or an organic group with up to 50 carbon atoms, and
    wherein, alternatively, $R^{2b}$, $R^{4b}$, and the two carbon atoms of the monothiocarbonate group together form a five to ten membered carbon ring, and
    wherein one of the groups $R^{1b}$ to $R^{4b}$ is a linking group to Z,
    n is an integral number of at least 2, and
    Z is a n-valent organic group.

3. The process according to claim 1, wherein the compound B) comprises one to five amino groups.

4. The process according to claim 1, wherein the at least one functional group of compound C) that reacts with —SH is a non-aromatic, ethylenically unsaturated group.

5. The process according to claim 1, wherein the compound B) or compound C), if present, comprises the silicon-functional group.

6. The process according to claim 1, wherein the silicon-functional group is an alkoxysilane group of formula (III),

wherein two or three of the groups $R^{1s}$ to $R^{3s}$ are an alkoxy group, and the remaining group $R^{1s}$ to $R^{3s}$ is an alkyl group, a vinyl group, or an allyl group.

7. The process according to claim 1, wherein at least one of the compounds A), B), or optionally C) comprises a segment selected from the group consisting of a polyether group and an organic polysulfide group.

8. The process according to claim 1, wherein a mixture of the compounds A), B), and optionally C) is liquid at 21° C. and 1 bar.

9. The process according to claim 1, wherein a content of silicon in the prepolymer is 0.001 to 0.3 mol silicon per 100 g of the prepolymer.

10. A prepolymer comprising a urethane group and a curable silicon-functional group, obtainable by the process as defined in claim 1.

11. The prepolymer according to claim 10, further comprising:
a group of formula (IV),

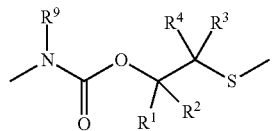

wherein
$R^1$ is $R^{1a}$ or $R^{1b}$,
$R^2$ is $R^{2a}$ or $R^{2b}$,
$R^3$ is $R^{3a}$ or $R^{3b}$,
$R^4$ is $R^{4a}$ or $R^{4b}$,
$R^{1a}$ to $R^{4a}$ independently from one another are hydrogen or an organic group with up to 50 carbon atoms, or, alternatively, $R^{2a}$, $R^{4a}$ and the two linking carbon atoms together form a five to ten membered carbon ring;
$R^{1b}$ to $R^{4b}$ independently from one another are hydrogen or an organic group with up to 50 carbon atoms, wherein, alternatively, $R^{2b}$, $R^{4b}$ and the two carbon atoms of the monothiocarbonate group together form a five to ten membered carbon ring,
one of the groups $R^{1b}$ to $R^{4b}$ is a linking group to Z,
n is an integral number of at least 2,
Z is a n-valent organic group, and
$R^9$ is hydrogen, $C_1$-$C_4$-alkyl, or $C_1$-$C_4$-alkylene-N($C_1$-$C_4$alkyl)$_2$; and
a curable silicon-functional group.

12. The prepolymer according to claim 11, wherein the silicon-functional group is a group of formula (III),

wherein two or three of the groups $R^{1s}$ to $R^{3s}$ are an alkoxy group, and the remaining group $R^{1s}$ to $R^{3s}$ is an alkyl group, a vinyl group, or an allyl group.

13. The prepolymer according to claim 11, wherein the prepolymer comprises a segment (c) selected from the group consisting of a polyether group and an organic polysulfide group.

14. The prepolymer according to claim 12, comprising:
a group of formula (V),

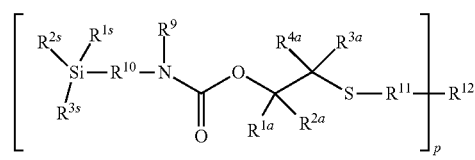

wherein
$R^9$ is hydrogen, $C_1$-$C_4$-alkyl, or $C_1$-$C_4$-alkylene-N($C_1$-$C_4$alkyl)$_2$,
$R^{10}$ is a $C_1$-$C_{18}$-alkylene group, which is optionally interrupted by O, S, or $NR^{13}$,
$R^{11}$ is a group derived from a non-aromatic, ethylenically unsaturated group,
$R^{12}$ is a p-valent polyether or an organic polysulfide group;
$R^{13}$ is hydrogen or $C_1$-$C_4$-alkyl; and
p is an integral number of 2 to 6;
or a group of formula (VI),

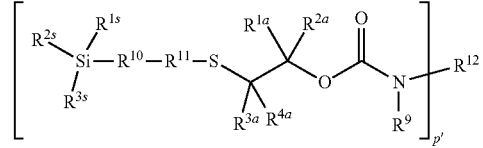

wherein
$R^9$ is hydrogen or $C_1$-$C_4$-alkyl,
$R^{10}$ is a $C_1$-$C_{18}$-alkylene group, which is optionally interrupted by O, S, or $NR^{13}$,
$R^{11}$ is a group derived from a non-aromatic, ethylenically unsaturated group,
$R^{12}$ is a p'-valent polyether group or an organic polysulfide group;
$R^{13}$ is hydrogen or $C_1$-$C_4$-alkyl; and
p' is an integral number of 2 to 5.

15. A composition comprising the prepolymer as defined in claim 11.

16. A one-component sealant or adhesive composition, comprising the prepolymer according claim 11.

17. The prepolymer according to claim 13, wherein the prepolymer comprises the segment (c) in an amount of from 50 to 95 wt %, based on a total weight of the prepolymer.

18. The prepolymer according to claim 11, wherein the prepolymer is applied to a surface, gap, or a three-dimensional template, and the curable silicon-functionalized group is cured with ambient water.

* * * * *